(12) United States Patent
Avni et al.

(10) Patent No.: US 9,737,201 B2
(45) Date of Patent: *Aug. 22, 2017

(54) APPARATUS AND METHOD FOR LIGHT CONTROL IN AN IN-VIVO IMAGING DEVICE

(71) Applicant: GIVEN IMAGING LTD., Yoqneam (IL)

(72) Inventors: Dov Avni, Haifa (IL); Arkady Glukhovsky, Santa Clarita, CA (US)

(73) Assignee: GIVEN IMAGING LTD., Yoqneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/830,848

(22) Filed: Aug. 20, 2015

(65) Prior Publication Data

US 2015/0351619 A1  Dec. 10, 2015

Related U.S. Application Data

(63) Continuation of application No. 10/551,053, filed as application No. PCT/IL2004/000265 on Mar. 23, 2004, now Pat. No. 9,149,175, and a continuation-in-part of application No. 10/202,608, filed on Jul. 25, 2002, now abandoned.

(60) Provisional application No. 60/307,603, filed on Jul. 26, 2001.

(30) Foreign Application Priority Data

Mar. 23, 2003 (IL) .......................................... 155046

(51) Int. Cl.
*A61B 5/05* (2006.01)
*A61B 1/06* (2006.01)
*A61B 1/00* (2006.01)
*A61B 1/04* (2006.01)
*A61B 1/045* (2006.01)
*A61B 1/273* (2006.01)

(52) U.S. Cl.
CPC ........ *A61B 1/0684* (2013.01); *A61B 1/00006* (2013.01); *A61B 1/00009* (2013.01); *A61B 1/00057* (2013.01); *A61B 1/041* (2013.01); *A61B 1/045* (2013.01); *A61B 1/2736* (2013.01)

(58) Field of Classification Search
None
See application file for complete search history.

(56) References Cited

U.S. PATENT DOCUMENTS

| 5,807,261 A * | 9/1998 | Benaron ............... A61B 5/0086 |
| | | 600/473 |
| 6,364,829 B1 * | 4/2002 | Fulghum ............ A61B 1/00009 |
| | | 600/160 |
| 6,667,765 B1 * | 12/2003 | Tanaka ................. H04N 5/2353 |
| | | 348/229.1 |

FOREIGN PATENT DOCUMENTS

| JP | 11-111795 | 4/1999 |
| JP | 2002-112118 | 4/2002 |

* cited by examiner

*Primary Examiner* — Joel F Brutus
(74) *Attorney, Agent, or Firm* — Pearl Cohen Zedek Latzer Baratz LLP

(57) ABSTRACT

A device and method for example operating an in vivo imaging device wherein the illumination is operated at a certain rate or range of rates, and images are transmitted from the device.

12 Claims, 12 Drawing Sheets

APPARATUS AND METHOD FOR LIGHT CONTROL IN AN IN-VIVO IMAGING DEVICE

RELATED APPLICATION DATA

The present application is a continuation of U.S. application Ser. No. 10/551,053, entitled "Apparatus And Method For Light Control In An In-Vivo Imaging Device" filed on Sep. 23, 2005, which is a national phase of International App. PCT/IL2004/000265, filed on Mar. 23, 2004, which in turn claims priority from Israel patent application 155046, filed on Mar. 23, 2003; in addition U.S. application Ser. No. 10/551,053 is a continuation-in-part of U.S. patent application Ser. No. 10/202,608, filed Jul. 25, 2002, which in turn claims priority from U.S. Provisional Application 60/307,603, filed Jul. 26, 2001, all of which are incorporated by reference in their entirety.

BACKGROUND OF THE INVENTION

Devices and methods for performing in-vivo imaging of passages or cavities within a body are known in the art. Such devices may include, inter alia, various endoscopic imaging systems and devices for performing imaging in various internal body cavities.

Reference is now made to FIG. 1 which is a schematic diagram illustrating an embodiment of an autonomous in-vivo imaging device. The device 10A typically includes an optical window 21 and an imaging system for obtaining images from inside a body cavity or lumen, such as the GI tract. The imaging system includes an illumination unit 23. The illumination unit 23 may include one or more discrete light sources 23A, or may include only one light source 23A. The one or more light sources 23A may be a white light emitting diode (LED), or any other suitable light source, known in the art. The device 10A includes a CMOS imaging sensor 24, which acquires the images and an optical system 22 which focuses the images onto the CMOS imaging sensor 24. The illumination unit 23 illuminates the inner portions of the body lumen through an optical window 21. Device 10A further includes a transmitter 26 and an antenna 27 for transmitting the video signal of the CMOS imaging sensor 24, and one or more power sources 25. The power source(s) 25 may be any suitable power sources such as but not limited to silver oxide batteries, lithium batteries, or other electrochemical cells having a high energy density, or the like. The power source(s) 25 may provide power to the electrical elements of the device 10A.

Typically, in the gastrointestinal application, as the device 10A is transported through the gastrointestinal (GI) tract, the imager, such as but not limited to the multi-pixel CMOS sensor 24 of the device 10A acquires images (frames) which are processed and transmitted to an external receiver/recorder (not shown) worn by the patient for recording and storage. The recorded data may then be downloaded from the receiver/recorder to a computer or workstation (not shown) for display and analysis. Other systems and methods may also be suitable.

During the movement of the device 10A through the GI tract, the imager may acquire frames at a fixed or at a variable frame acquisition rate. For example, the imager (such as, but not limited to the CMOS sensor 24 of FIG. 1) may acquire images at a fixed rate of two frames per second (2 Hz). However, other different frame rates may also be used, depending, inter alia, on the type and characteristics of the specific imager or camera or sensor array implementation that is used, and on the available transmission bandwidth of the transmitter 26. The downloaded images may be displayed by the workstation by replaying them at a desired frame rate. According to this implementation, the expert or physician examining the data may be provided with a movie-like video playback, which may enable the physician to review the passage of the device through the GI tract.

One of the limitations of electronic imaging sensors is that they may have a limited dynamic range. The dynamic range of most existing electronic imaging sensors is significantly lower than the dynamic range of the human eye. Thus, when the imaged field of view includes both dark and bright parts or imaged objects, the limited dynamic range of the imaging sensor may result in underexposure of the dark parts of the field of view, or overexposure of the bright parts of the field of view, or both.

Various methods may be used for increasing the dynamic range of an imager. Such methods may include changing the amount of light reaching the imaging sensor, such as for example by changing the diameter of an iris or diaphragm included in the imaging device to increase or decrease the amount of light reaching the imaging sensor, methods for changing the exposure time, methods for changing the gain of the imager or methods for changing the intensity of the illumination. For example, in still cameras, the intensity of the flash unit may be changed during the exposure of the film.

When a series of consecutive frames is imaged such as in video cameras, the intensity of illumination of the imaged field of view within the currently imaged frame may be modified based on the results of measurement of light intensity performed in one or more previous frames. This method is based on the assumption that the illumination conditions do not change abruptly from one frame to the consecutive frame.

However, in an in vivo imaging device, for example, for imaging the GI tract, which may operate at low frame rates and which is moved through a body lumen (e.g., propelled by the peristaltic movements of the intestinal walls), the illumination conditions may vary significantly from one frame to the next frame. Therefore, methods of controlling the illumination based on analysis of data or measurement results of previous frames may not be always feasible, particularly at low frame rates.

Therefore there is a need for an imaging device that provides more accurate illumination, possibly tailored to particular in-vivo illumination requirements or environmental conditions.

SUMMARY OF THE INVENTION

Some embodiments of the present invention include a device and method for operating an in vivo imaging device wherein the illumination produced by the device may be varied in intensity and/or duration according to, for example, the amount of illumination produced by the device, which is reflected back to the device. In such a manner, the illumination can be controlled and made more efficient.

According to some embodiments of the present invention, a method for implementing light control in an in vivo device is provided. Accordingly, the parameters such as exposure time and/or the gain factor, or other parameters, for transmitting the recorded light may be altered. For example, the gain factor may be altered as a function of a light saturation level measured at at least one interval within the frame exposure period. In such a manner the in vivo device can prevent cases of over and under exposure, in addition to helping to ensure that exposure ceases after full exposure is attained.

According to some embodiments of the present invention, a method is provided for detecting problematic pixels in an imaging device. This method may enable defining and/or excluding problematic or non-functional pixels, for example based on an initial short exposure that enables a threshold saturation level to be reached only for problematic pixels.

According to some embodiments of the present invention, a method is provided for determining when an in vivo imaging device has entered a particular part of a body. Accordingly, environmental measurement devices may be used to detect environmental parameters, such as pH levels and temperature levels etc. Results recorded from these measurement devices may be used to define areas, regions, organs etc. wherein the in vivo device may be or may have been located. The device mode may be changed in accordance with the resulting definition.

According to some embodiments of the present invention, a method is provided for determining when an in vivo imaging device has entered a body, using dark frames. For example, when dark frames require substantial gain factor to attain full exposure, the device may be defined as being inside a body (a dark environment). The device mode may be changed in accordance with the resulting definition.

BRIEF DESCRIPTION OF THE DRAWINGS

The present invention is herein described, by way of example only, with reference to the accompanying drawings, in which like components are designated by like reference numerals, it being understood that these drawings are given for illustrative purposes only and are not meant to be limiting, wherein.

DETAILED DESCRIPTION OF THE INVENTION

Various aspects of the present invention are described herein. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Some embodiments of the present invention are based, inter alia, on controlling the illumination provided by the in-vivo imaging device based on light measurement which is performed within the duration of a single frame acquisition time or a part thereof.

It is noted that while the embodiments of the invention shown hereinbelow are adapted for imaging of the gastrointestinal (GI) tract, the devices and methods disclosed herein may be adapted for imaging other body cavities or spaces.

Figure 1:
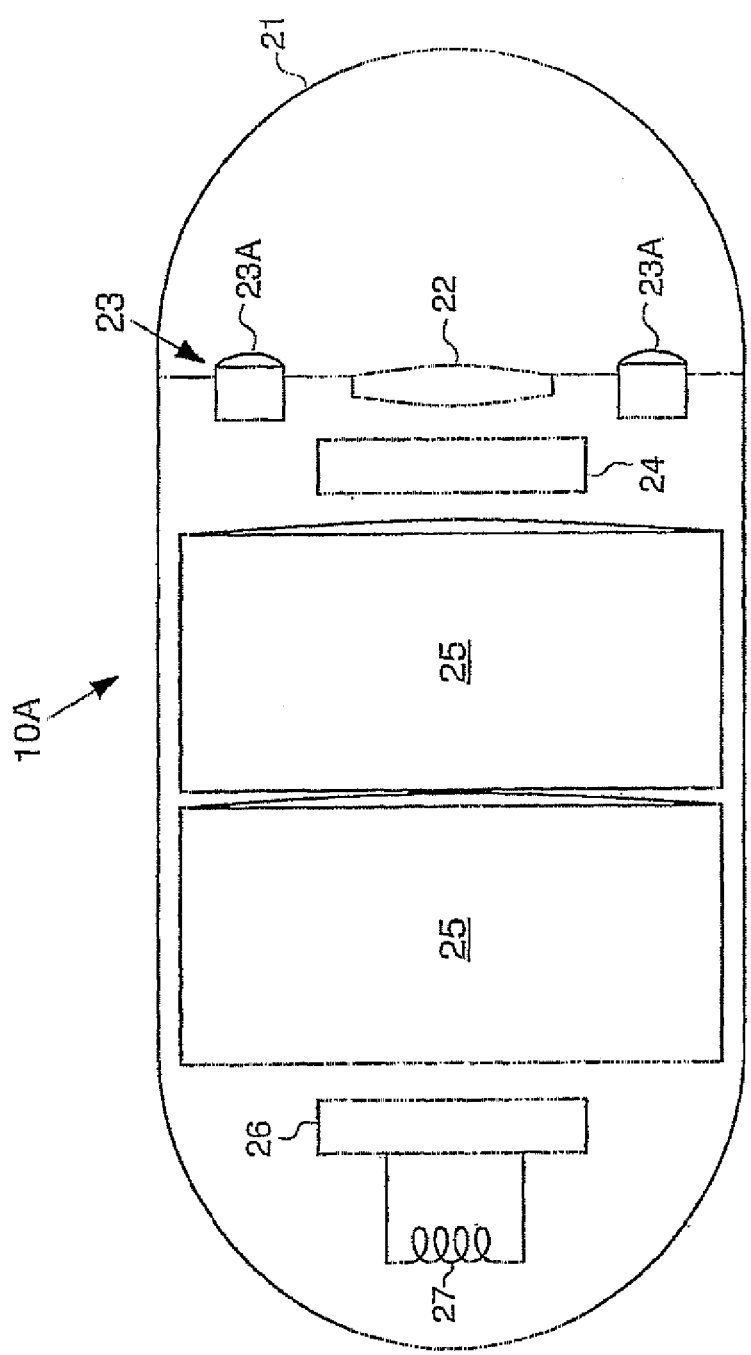
FIG. 1 is a schematic diagram illustrating an embodiment of a prior art autonomous in-vivo imaging device.
Figure 2:
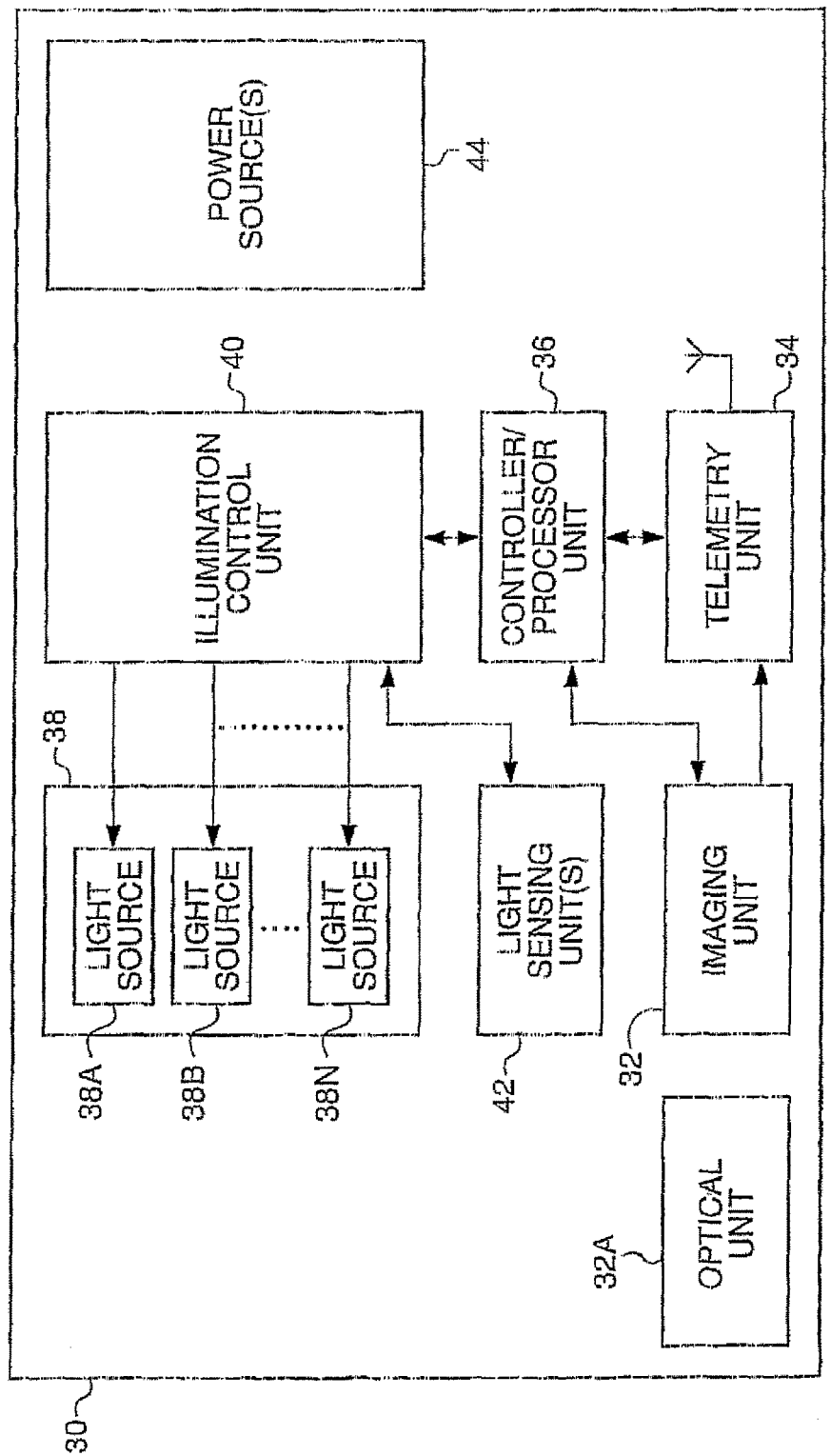
FIG. 2 is a schematic block diagram illustrating part of an in-vivo imaging device having an automatic illumination control system, in accordance with an embodiment of the present invention.

Reference is now made to FIG. 2 which is a schematic block diagram illustrating part of an in-vivo imaging device having an automatic illumination control system, in accordance with an embodiment of the present invention. The device 30 may be constructed as a swallowable video capsule as disclosed for the device 10A of FIG. 1 or in U.S. Pat. No. 5,604,531 to Iddan et al., or in Co-pending PCT Patent Application, Publication no. WO 01/65995 to Glukhovsky et al, both hereby incorporated by reference in their entirety. However, the system and method of the present invention may be used in conjunction with other in-vivo imaging devices.

The device 30 may include an imaging unit 32 adapted for imaging the GI tract. The imaging unit 32 may include an imaging sensor (not shown in detail), such as but not limited to the CMOS imaging sensor 24 of FIG. 1. However, the imaging unit 32 may include any other suitable type of imaging sensor known in the art. The imaging unit 32 may also include an optical unit 32A including one or more optical elements (not shown), such as one or more lenses (not shown), one or more composite lens assemblies (not shown), one or more suitable optical filters (not shown), or any other suitable optical elements (not shown) adapted for focusing an image of the GI tract on the imaging sensor as is known in the art and disclosed hereinabove with respect to the optical unit 22 of FIG. 1.

The optical unit 32A may include one or more optical elements (not shown) which are integrated with the imaging unit 32, such as for example, a lens (not shown) which is attached to, or mounted on, or fabricated on or adjacent to the imager light sensitive pixels (not shown) as is known in the art.

The device 30 may also include a telemetry unit 34 suitably connected to the imaging unit 32 for telemetrically transmitting the images acquired by the imaging unit 32 to an external receiving device (not shown), such as but not limited to the receiver/recorder device disclosed in U.S. Pat. No. 5,604,531 to Iddan et al., or in Co-pending PCT Patent Application, Publication No. WO 01/65995 to Glukhovsky et al.

The device 30 may also include a controller/processor unit 36 suitably connected to the imaging unit 32 for controlling the operation of the imaging unit 32. The controller/processor unit 36 may comprise any suitable type of controller, such as but not limited to, an analog controller, a digital controller such as, for example, a data processor, a microprocessor, a micro-controller, or a digital signal processor (DSP). The controller/processor unit 36 may also comprise hybrid analog/digital circuits as are known in the art. The controller/processor unit 36 may be suitably connected to the telemetry unit 34 for controlling the transmission of image frames by the telemetry unit 34.

The controller/processor unit 36 may be (optionally) suitably connected to the imaging unit 32 for sending control signals thereto. The controller/processor unit 36 may thus (optionally) control the transmission of image data from the imaging unit 32 to the telemetry unit 34.

The device 30 may include an illuminating unit 38 for illuminating the GI tract. The illuminating unit 38 may include one or more discrete light sources 38A, 38B, to 38N or may include only one light source; such light source(s) may be, for example, but are not limited to, the light sources 23A of FIG. 1. The light source(s) 38A, 38B, to 38N of the illuminating unit 38 may be white light emitting diodes, such as the light sources disclosed in co-pending PCT Patent Application, Publication No. WO 01/65995 to Glukhovsky et al. However, the light source(s) 38A, 38B, 38N of the illuminating unit 38 may also be any other suitable light source, known in the art, such as but not limited to incandescent lamp(s), flash lamp(s) or gas discharge lamp(s), or any other suitable light source(s).

It is noted that, in accordance with another embodiment of the present invention, the in vivo imaging device may include a single light source (not shown).

The device 30 may also include an illumination control unit 40 suitably connected to the light sources 38A, 38B, to 38N of the illuminating unit 38 for controlling the energizing of the light sources 38A, 38B, to 38N of the illuminating unit 38. The illumination control unit 40 may be used for switching one or more of the light sources 38A, 38B, to 38N on or off, and/or for controlling the intensity of the light produced by one or more of the light sources 38A, 38B, to 38N, as is disclosed in detail hereinafter.

The controller/processor unit 36 may be suitably connected to the illumination control unit 40 for (optionally) sending control signals thereto. Such control signals may be used for synchronizing or timing the energizing of the light sources 38A, 38B, 38N within the illuminating unit 38, relative to the imaging cycle or period of the imaging unit 32. The illumination control unit 40 may be (optionally) integrated within the controller/processor unit 36, or may be a separate controller. In some embodiments, illumination control unit 40 and/or controller/processor unit 36 may be part of telemetry unit 34.

The device 30 may further include a light sensing unit(s) 42 for sensing the light produced by the illuminating unit 38 and reflected from the walls of the GI tract. The light sensing unit(s) 42 may comprise a single light sensitive device or light sensor, or a plurality of discrete light sensitive device(s) or light sensor(s), such as but not limited to, a photodiode, a phototransistor, or the like. Other types of light sensors known in the art and having suitable characteristics may also be used for implementing the light sensing unit or units of embodiments of the present invention.

The light sensing unit(s) 42 may be suitably connected to the illumination control unit 40 for providing the illumination control unit 40 with a signal representative of the intensity of the light reflected from the walls of the gastrointestinal tract (or any other object within the field of view of the imaging unit 32). In operation, the illumination control unit 40 may process the signal received from the light sensing unit(s) 42 and, based on the processed signal, may control the operation of the light source(s) 38A, 38B, to 38N as is disclosed in detail hereinabove and hereinafter.

The device 30 may also include a power source 44 for providing power to the various components of the device 30. It is noted that for the sake of clarity of illustration, the connections between the power source 44 and the circuits or components of the device 30 which receive power therefrom, are not shown in detail. The power source 44 may be, for example, an internal power source similar to the power source(s) 25 of the device 10A, e.g., a battery or other power source. However, if the device 30 is configured as an insertable device (such as, for example, an endoscope-like device or a catheter-like device, or any other type of in vivo imaging device known in the art), the power source 44 may also be an external power source which may be placed outside the device 30 (such an external configuration is not shown in FIG. 2 for the sake of clarity of illustration). In such an embodiment having an external power source (not shown), the external power source (not shown) may be connected to the various power requiring components of the imaging device through suitable electrical conductors (not shown), such as insulated wires or the like.

It is noted that while for autonomous or swallowable in-vivo imaging device such as the device 10A the power source(s) 25 are preferably (but not necessarily) compact power sources for providing direct current (DC), external power sources may be any suitable power sources known in the art, including but not limited to power sources providing alternating current (AC) or direct current or may be power supplies couples to the mains as is known in the art.

The various functions and processes implemented by the swallowable in-vivo imaging device may be executed by, for example, a processor unit (e.g., unit 36 in FIG. 2). These functions and processes may be implemented by the processor unit 36 alone, and/or by alternative units, such as illumination control unit 40, telemetry unit 34, light sensing units 42, imaging unit 32 etc., or any combination of units. The various units may optionally be integrated within the processor unit 36, such that the processor unit can be said to implement any of the functions and processes herein described. The methods and processes described may be also embodied in other sensing devices having other structures and other components.

Figure 4:
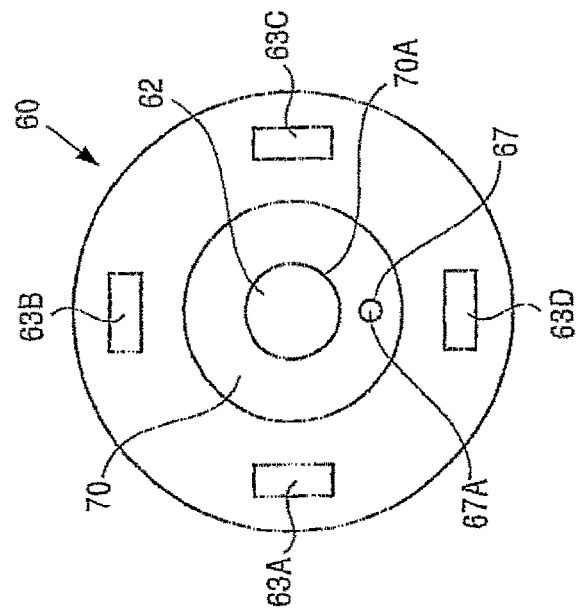
FIG. 4 is a schematic front view of the device illustrated in FIG. 3.
Figure 3:
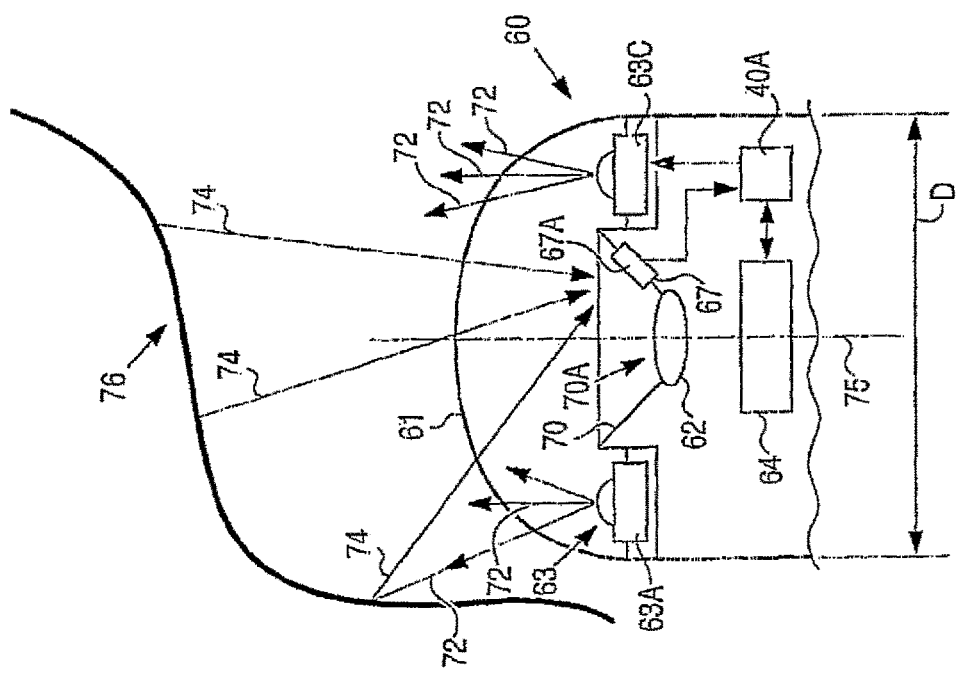
FIG. 3 is a schematic cross-sectional view of part of an in-vivo imaging device having an automatic illumination control system and four light sources, in accordance with an embodiment of the present invention.

Reference is now made to FIGS. 3 and 4. FIG. 3 is a schematic cross-sectional view of part of an in-vivo imaging device having an automatic illumination control system and four light sources, in accordance with an embodiment of the present invention. FIG. 4 is a schematic front view of the device illustrated in FIG. 3.

The device 60 (only part of which is shown in FIG. 3) includes an imaging unit 64. The imaging unit 64 may be similar to the imaging unit 32 of FIG. 2 or to the imaging unit 24 of FIG. 1. Preferably, the imaging unit 64 may be a CMOS imaging unit, but other different types of imaging units may be also used. The imaging unit 64 may include CMOS imager circuitry, as is known in the art, but may also include other types of support and or control circuitry therein, as is known in the art and disclosed, for example, in U.S. Pat. No. 5,604,531 to Iddan et al., or in Co-pending PCT Patent Application, Publication No. WO 01/65995 to Glukhovsky et al. The device 60 also includes an optical unit 62 which may comprise a lens or a plurality of optical elements as disclosed hereinabove for optical unit 22 of FIG. 1 and the optical unit 32A of FIG. 2.

The device 60 may include an illuminating unit 63, which may include four light sources 63A, 63B, 63C and 63D which may be disposed within the device 60 as shown in FIG. 4. The light sources 63A, 63B, 63C and 63D may be the white LED light sources or as disclosed, for example, in Co-pending US patent application, PCT Patent Application, Publication No. WO 01/65995 to Glukhovsky et al., but may also be any other suitable type of light sources, including but not limited to, infrared light sources, monochromatic light sources, band limited light sources known in the art or disclosed hereinabove.

It is noted that while in accordance with one embodiment of the present invention the light sources 63A, 63B, 63C and 63D are shown to be identical, other embodiments of the invention may be implemented with multiple light sources which may not be identical. Some of the light sources may have a spectral distribution, which is different than the spectral distribution of the other light sources. For example, of the light sources within the same device, one of the light sources may be a red LED, another light source may be a blue LED and another light source may be a yellow LED. Other configurations of light sources are also possible.

The device 60 may also include a baffle 70, which may be conically shaped or which may have any other suitable shape. The baffle 70 may have an aperture 70A therein. The baffle 70 may be interposed between the light sources 63A, 63B, 63C and 63D and the optical unit 62 and may reduce the amount of light coming directly from the light sources 63A, 63B, 63C and 63D to enter the aperture 70A. The device 60 may include a transparent optical dome 61 similar to the optical dome 21 of FIG. 1. The optical dome 61 may be made from a suitable transparent plastic material or glass or from any other suitable material which is sufficiently transparent to at least some of the wavelengths of light produced by the light sources 63A, 63B, 63C and 63D to allow for adequate imaging.

The device 60 may further include at least one light sensing unit 67 for sensing light, which is reflected from or diffused by the intestinal wall 76. The light sensing unit may be attached to the baffle 70 such that its light sensitive part 67A faces the optical dome 61. Preferably, but not necessarily, the light sensing unit 67 may be positioned on the surface of baffle 70 at a position which allows the light sensing unit 67 to sense an amount of light which is representative or proportional to the amount of light entering the aperture 70A of the baffle 70. This may be true when the illuminated object is semi-diffusive (as the intestinal surface may be), and when the size of the light sensing unit 67 and its distance from the imaging sensor axis 75 are small compared to the diameter D of the capsule like device 60.

The device 60 (FIG. 3) is illustrated as being adjacent to the intestinal wall 76. In operation, light rays 72 which are generated by the light sources 63A, 63B, 63C and 63D may penetrate the optical dome 61 and may be reflected from the intestinal wall 76. Some of the reflected light rays 74 may reach the light-sensing unit 67. Other reflected light rays (not shown) may reach the aperture 70A and pass the optical unit 62 to be focused on the imaging unit 64.

The amount of light measured by the light-sensing unit 67 may be proportional to the amount of light entering the aperture 70A. Thus, the measurement of the light intensity reaching the light sensing unit 67 may be used to determine the light output of the light sources 63A, 63B, 63C and 63D as is disclosed in detail hereinafter.

The device 60 also includes an illumination control unit 40A. The illumination control unit 40A is suitably coupled to the light sensing unit 67 and to the illuminating unit 63. The illumination control unit 40A may process the signal received from the light sensing unit 67 to control the light sources 63A, 63B, 63C and 63D as is disclosed in detail hereinafter.

The device 60 may also include a wireless transmitter unit (not shown in FIG. 3) and an antenna (not shown in FIG. 3), such as but not limited to the transmitter 26 and the antenna 27 of FIG. 1 or may include any suitable telemetry unit (such as, but not limited to the telemetry unit 34 of FIG. 2). The telemetry unit may be a transmitter or a transceiver, for wirelessly transmitting (and optionally also receiving) data and control signals to (and optionally from) an external receiver/recorder (not shown in FIG. 3) as disclosed in detail hereinabove. The device 60 may also include one or more power sources such as, for example, the power sources 25 of FIG. 1, or any other suitable power sources, known in the art.

Figure 5:
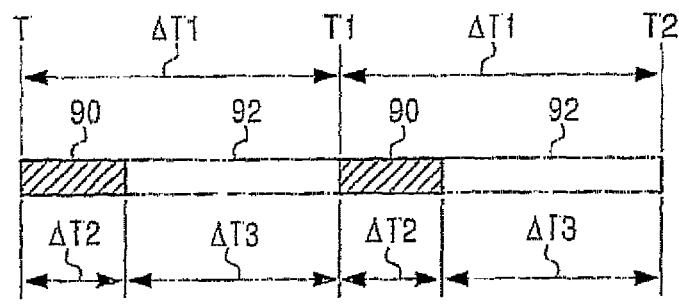
FIG. 5 is a schematic diagram illustrating a method of timing of the illumination and image acquisition in an in vivo imaging device having a fixed illumination duration, according to an embodiment of the invention.

Reference is now made to FIG. 5 which is a schematic diagram illustrating a method of timing of the illumination and image acquisition in an in vivo imaging device having a fixed illumination duration. The timing method may be characteristic for imaging devices having CMOS imagers but may also be used in devices having other types of imagers.

An image acquisition cycle or period starts at the time T. The first image acquisition cycle ends at time T1 and has a duration ΔT1. The second image acquisition cycle starts at time T1, ends at time T2 and has a duration ΔT1. Each imaging cycle or period may comprise two parts, an illumination period 90 having a duration ΔT2, and a dark period 92 having a duration ΔT3. The illumination periods 90 are represented by the hashed bars of FIG. 5. During the illumination period 90 of each imaging cycle, the illumination unit (such as but not limited to the illuminating unit 38 of FIG. 2, or the illuminating unit 63 of FIG. 3) is turned on and provides light for illuminating the intestinal wall. During the dark period 92 of each imaging cycle, the illuminating unit (such as but not limited to the illuminating unit 38 of FIG. 2, or the illuminating unit 63 of FIG. 3) is switched off and does not provide light.

The dark period 92, or a part thereof, may be used for, for example, acquiring an image from the imager by, for example, scanning the pixels of the imager and for processing the imager output signals and for transmitting the output signals or the processed output signals to an external receiver or receiver/recorder device, as disclosed hereinabove.

It is noted that while for the sake of simplicity, the diagram of FIG. 5 illustrates a case in which the image acquisition cycle duration is fixed, and imaging is performed at a fixed frame rate, this is not mandatory. Thus, the frame rate and therefore the image acquisition cycle duration may vary during imaging in accordance with a measured parameter such as, for example the velocity of the imaging device within the gastrointestinal tract.

Generally, different types of light control methods may be used for ensuring adequate image acquisition.

In a first method, the amount of light impinging on the light sensing unit 67 may be continuously measured and recorded during the illumination of the target tissue by the illuminating unit 63 to provide a cumulative value representative of the total cumulative number of photons detected by the light sensing unit 67. When this cumulative value reaches a certain value, the illuminating unit 63 may be shut off by switching off the light sources 63A, 63B, 63C, and 63D included in the illuminating unit 63. In this way the device 60 may ensure that when the quantity of measured light is sufficient to result in an adequately exposed frame (on the average), the illuminating unit 63 is turned off.

One advantage of the first method is that if the light sources (such as the light sources 63A, 63B, 63C, and 63D) are operated at their maximal or nearly maximal light output capacity, the switching off may save energy when compared to the energy expenditure in a fixed duration illumination period (such as the illumination period 90 of FIG. 5).

Another advantage of the first method is that it enables the shortening of the duration of the illumination period within the imaging cycle in comparison with using a fixed illumination period. In a moving imaging device, such as the device 60, ideally, it may be desirable to have the illumination period as short as practically possible, since this prevents or reduces image smearing due to the movement of the device 60 within the GI tract. Thus, typically, in a moving imaging device, the shorter the illumination period, the sharper will the resulting image be (assuming that enough light is generated by the illuminating unit to ensure adequate imager exposure).

This may be somewhat similar to the increasing of the shutter speed in a regular shutter operated camera in order to decrease the duration of exposure to light to prevent smearing of the image of a moving object or image, except that in embodiments of the present method there is typically no shutter and the illumination period is being shortened controllably to reduce image smearing due to device movements in the GI tract.

Figure 6:
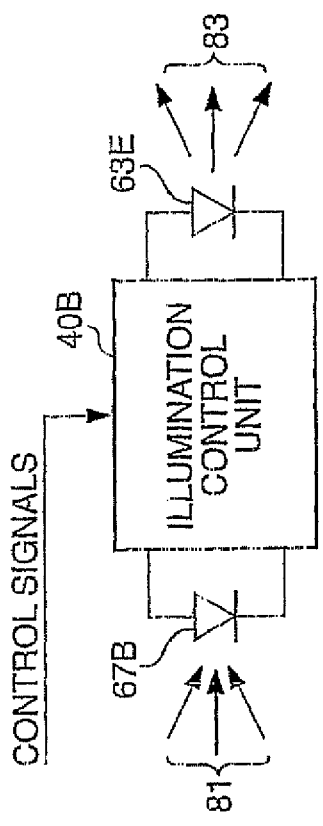
FIG. 6 is a schematic diagram illustrating one possible configuration for an illumination control unit coupled to a light sensing photodiode and to a light emitting diode, in accordance with an embodiment of the present invention.
Figure 7:
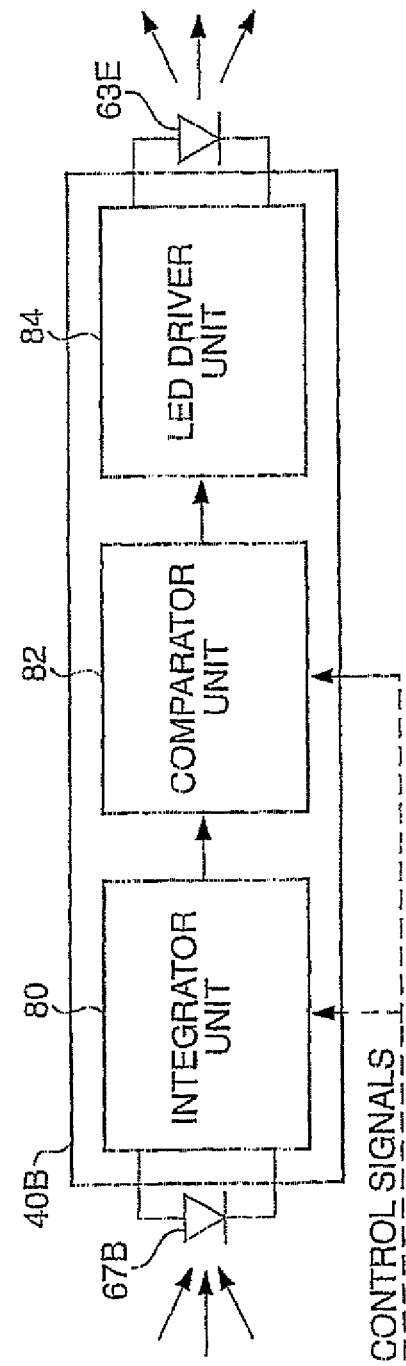
FIG. 7 is a schematic diagram illustrating the illumination control unit of FIG. 6 in detail, in accordance with an embodiment of the present invention.

Reference is now made to FIGS. 6 and 7. FIG. 6 is a schematic diagram illustrating one possible configuration for an illumination control unit coupled to a light sensing photodiode and to a light emitting diode, in accordance with an embodiment of the present invention. FIG. 7 is a schematic diagram illustrating the illumination control unit of FIG. 6 in detail, in accordance with an embodiment of the present invention.

The illumination control unit 40B of FIG. 6 may be suitably connected to a photodiode 67B, which may be operated as a light sensing unit. Any other suitable sensing unit or light sensor may be used. The illumination control unit 40B may be suitably connected to a light emitting diode (LED) 63E. The LED 63E may be a white LED as disclosed hereinabove or may be any other type of LED suitable for illuminating the imaged target (such as the gastrointestinal wall). The illumination control unit 40B may receive a current signal from the photodiode 67B. The received signal may be proportional to the intensity of light (represented schematically by the arrows 81) impinging the photodiode 67B. The illumination control 40B may process the received signal to determine the amount of light that illuminated the photodiode 67B within the duration of a light measuring time period. The illumination control 40B may control the energizing of the LED 63E based on the amount of light that illuminated the photodiode 67B within the duration of the light measuring time period. Examples of the type of processing and control of energizing are disclosed in detail hereinafter. The illumination control unit 40B may also receive control signals from other circuitry components included in the in vivo imaging device. For example, the control signals may include timing and/or synchronization signals, on/off switching signals, reset signals, or the like.

The light sensing unit(s) and light producing unit(s) may be any suitable light producing or sensing units other than diodes.

FIG. 7 illustrates one possible embodiment of the illumination control unit 40B. The illumination control unit 40B may include, for example, an integrator unit 80, a comparator unit 82 and a LED driver unit 84. The integrator unit 80 is coupled to the photodiode 67B to receive therefrom a signal indicative of the intensity of the light impinging on the photodiode 67B, and to record and integrate the amount of light impinging on the photodiode 67B. The integrator unit 80 may be suitably connected to the comparator unit 82.

The integrator unit 80 may record and integrate the amount of light impinging on the photodiode 67B, integrating the received signal, and output an integrated signal to the comparator unit 82. The integrated signal may be proportional to or indicative of the cumulative number of photons hitting the photodiode 67B over the integration time period. The comparator unit 80 may be suitably connected to the LED driver unit 84. The comparator unit 80 may continuously compare the value of the integrated signal to a preset threshold value. When the value of the integrated signal is equal to the threshold value, the comparator unit 82 may control the LED driver unit 84 to switch off the power to the LED 63E and thus cease the operation of the LED 63E.

Thus, the illumination control unit 40A (of FIG. 3) may be constructed and operated similar to the illumination control unit 40B of FIGS. 6 and 7.

It is noted that while the circuits illustrated in FIG. 7 may be implemented as analog circuits, digital circuits and/or hybrid analog/digital circuits may be used in implementing the illumination control unit, as is disclosed in detail hereinafter (with respect to FIG. 11).

Figure 8:
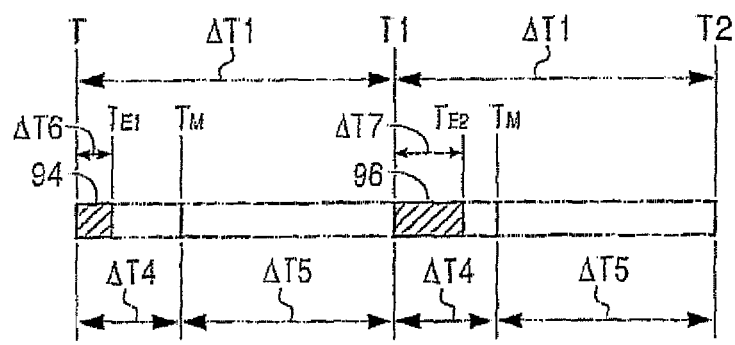
FIG. 8 is a schematic diagram useful for understanding a method of timing of the illumination and image acquisition in an in vivo imaging device having a variable controlled illumination duration, according to an embodiment of the invention.

Reference is now made to FIG. 8, which is a schematic diagram useful for understanding a method of timing of the illumination and image acquisition in an in vivo imaging device having a variable controlled illumination duration, according to one embodiment.

An image acquisition cycle or period starts at the time T. The first image acquisition cycle ends at time T1 and has a duration ΔT1. The second image acquisition cycle starts at time T1, ends at time T2 and has a duration ΔT1. In each imaging cycle, the time period having a duration ΔT4 defines the maximal allowable illumination period. The maximal allowable illumination period ΔT4 may typically be a time period which is short enough as to enable imaging without excessive image smearing or blurring due to the movement of the device 60 within the GI tract. The time $T_M$ is the time of the end of the maximal allowable illumination period ΔT4 relative to the beginning time of the first imaging cycle.

The maximal allowable illumination period ΔT4 may be factory preset taking into account, inter alia, the typical or average (or maximal) velocity reached by the imaging device within the GI tract, (as may be determined empirically in a plurality of devices used in different patients), the type of the imaging sensor (such as, for example, the CMOS sensor 64 of the device 50) and its scanning time requirements, and other manufacturing and timing considerations. In accordance with one implementation of the invention, when imaging at 2 frames per second ΔT1=0.5 second, the duration of ΔT4 may be set to have a value in the range of 20-30 milliseconds. However, this duration is given by way of example only, and ΔT4 may have other different values. Typically, the use of a maximal allowable illumination period ΔT4 of less than 30 milliseconds may result in acceptable image quality of most of the acquired image frames without excessive degradation due to blurring of the image resulting from movement of the imaging device within the GI tract.

The time period ΔT5 is defined as the difference between the entire imaging cycle duration ΔT1 and the maximal allowable illumination period ΔT4 (ΔT5=ΔT1−ΔT4).

At the time of beginning T of the first imaging cycle, the illumination unit (such as but not limited to the illuminating unit 63 of FIG. 3) is turned on and provides light for illuminating the intestinal wall. The light sensing unit 67 senses the light reflected and/or diffused from the intestinal wall 76 and provides a signal to the illumination control unit 40A of the device 60. The signal may be proportional to the average amount of light entering the aperture 70A. The signal provided by the light sensing unit 67 may be integrated by the illumination control unit 40A as is disclosed in detail hereinabove with respect to the illumination control unit 40B of FIGS. 6 and 7.

The integrated signal may be compared to a preset threshold value (for example by a comparator such as the comparator unit 82 of FIG. 7). When the integrated signal is equal to the threshold value, the illumination control unit 40A ceases the operation of the light sources 63A, 63B, 63C and 63D of the illuminating unit 63. The time TE1 is the time at which the illuminating control unit turns off the light sources 63A, 63B, 63C and 63D within the first imaging cycle. The time interval beginning at time T and ending at time TE1 is the illumination period 94 (represented by the hashed bar labeled 94) for the first imaging cycle. The illumination period 94 has a duration of ΔT6. It may be seen that for the first imaging cycle ΔT6<ΔT4.

After the time TE1 the scanning of the pixels of the CMOS sensor 64 may begin and the pixel data (and possibly other data) may be transmitted by the transmitter (not shown in FIG. 3) or telemetry unit of the device 60.

Preferably, the scanning (read out) of the pixels of the CMOS sensor 64 may begin as early as the time TE1 of the termination of the illumination. For example the illumination control unit 40A may send a control signal to the CMOS sensor at time TE1 to initiate the scanning of the pixels of the CMOS sensor 64. However, the scanning of the pixels may also begin at a preset time after the time $T_M$ which is the ending time of the maximal allowable illumination period ΔT4, provided that sufficient time is available for pixel scanning and data transmission operations. According to one embodiment, keeping the start of readout time fixed, for example at $T_M$, may enable simpler implementation of the receiving unit.

At the time of beginning T1 of the second imaging cycle, the illuminating unit 63 is turned on again. The light sensing unit 67 senses the light reflected and/or diffused from the intestinal wall 76 and provides a signal to the illumination control unit 40A of the device 60. The signal may be proportional to the average amount of light entering the aperture 70A.

The signal provided by the light sensing unit 67 may be integrated and compared to the threshold value as disclosed hereinabove for the first imaging cycle. When the integrated signal is equal to the threshold value, the illumination control unit 40A turns off the light sources 63A, 63B, 63C and 63D of the illuminating unit 63. However, in the particular schematic example illustrated in FIG. 8, the intensity of light reaching the light sensing unit 67 in the second imaging cycle is lower than the intensity of light reaching the light sensing unit 67 in the first imaging cycle.

This difference of the illumination intensity or intensity versus time profile between different imaging cycle may be due to, inter alia, movement of the device 60 away from the intestinal wall 76, or a change of the position or orientation of the device 60 with respect to the intestinal wall 76, or a change in the light absorption or light reflecting or light diffusion properties of the part of the intestinal wall 76 which is within the field of view of the device 60.

Therefore it takes longer for the integrated signal output of the integrator unit to reach the threshold value. Therefore, the illumination control unit 40A turns the illuminating unit 63 off at a time TE2 (it is noted that TE2>TE1).

The time interval beginning at time T1 and ending at time TE2 is the illumination period 96 for the second imaging cycle. The illumination period 96 (represented by the hashed bar labeled 96) has a duration ΔT7. It may be seen that for the second imaging cycle ΔT7<ΔT4.

Thus, the duration of the illumination period within different imaging cycles may vary and may depend, inter alia, on the intensity of light reaching the light sensing unit 67.

After the time TE2 the scanning of the pixels of the CMOS sensor 64 may begin and the pixel data (and possibly other data) may be transmitted as disclosed in detail hereinabove for the first imaging cycle of FIG. 8.

It is noted that while for the sake of simplicity, the diagram of FIG. 8 illustrates a case in which the image acquisition cycle duration ΔT1 is fixed, and imaging is performed at a fixed frame rate, this is not mandatory. Thus, the frame rate and therefore the image acquisition cycle duration ΔT1 may vary during imaging in accordance with a measured parameter such as, for example the velocity of the imaging device within the gastrointestinal tract. In such cases, the duration of the imaging cycle may be shortened or increased in response to the measured velocity of the device 60 in order to increase or decrease the frame rate, respectively.

For example, co-pending U.S. patent application Ser. No. 09/571,326, filed May 15, 2000, co-assigned to the assignee of the present application, incorporated herein by reference in its entirety for all purposes, discloses, inter alia, a device and method for controlling the frame rate of an in-vivo imaging device.

The automatic illumination control methods disclosed hereinabove may be adapted for use in device having variable frame rate. Such adaptation may take into account the varying duration of the imaging cycle and the implementation may depend, inter alia, on the amount of time required to complete the pixel scanning and the data transmission, the available amount of power available to the device 60, and other considerations.

A simple way of adapting the method may be to limit the maximal frame rate of the imaging device, such that even when the maximal frame rate is being used, there will be enough time left for pixel scanning and data transmission within the time period.

Figure 9:
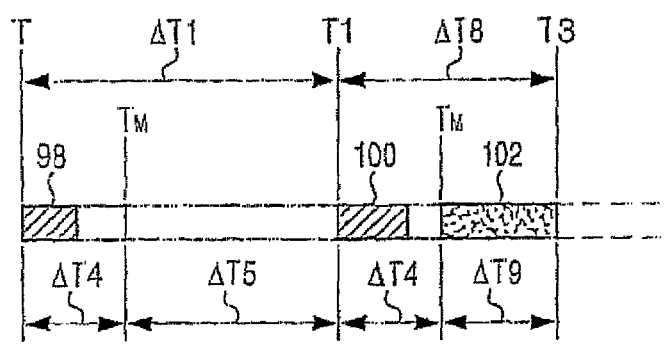
FIG. 9 is a schematic diagram useful for understanding a method of timing of the illumination and image acquisition in an in vivo imaging device having a variable frame rate and a variable controlled illumination duration according to an embodiment of the invention.

Reference is now made to FIG. 9, which is a schematic diagram useful for understanding a method of timing of the illumination and image acquisition in an in vivo imaging device having a variable frame rate and a variable controlled illumination duration.

The first imaging cycle of FIG. 9 is similar to the first imaging cycle of FIG. 8 except that the duration of the illumination period 98 of FIG. 9 (represented by the hashed bar labeled 98) is longer than the duration of the illumination period 94 of FIG. 8. The first imaging cycle of FIG. 9 starts at time T, ends at time T1, and has a duration $\Delta T1$. The time $T_M$ represents the end of the maximal allowable illumination period $\Delta T4$. The second imaging cycle of FIG. 9 begins at time T1 and ends at time T3. The duration of the second imaging cycle $\Delta T8$ is shorter than the duration of the first imaging cycle $\Delta T1$ ($\Delta T8 < \Delta T1$). The duration of the second imaging cycle $\Delta T8$ corresponds to the highest frame rate usable in the imaging device. The illumination period 100 of the second imaging cycle (represented by the hashed bar labeled 100 of FIG. 9) is timed by the illumination control unit depending on the light intensity as disclosed in detail hereinabove. The time period 102 (represented by the dotted bar labeled 102) represents the amount of time $\Delta T9$ required for scanning the pixels of the imager and transmitting the scanned frame data. $T_M$ represents the time of ending of the maximal allowable illumination period relative to the beginning time of each imaging cycle. Thus, if the frame rate is increased, even at the highest possible frame rate there is enough time to scan the pixels and transmit the data.

It is noted that typically, in an exemplary in vivo imaging device having a fixed frame rate, the time requited for scanning the pixels of a CMOS sensor having approximately 66,000 pixels (such as but not limited to a CMOS sensor arranged in a 256×256 pixel array), and for transmitting the digital (serial) data signals to an external receiver recorder may be approximately 0.4 seconds (assuming a scanning and data transmission time of approximately 6 microseconds per pixel). Thus, assuming a maximal illumination period of approximately 20-30 milliseconds, the frame rate may not be extended much higher than 2 frames per second. Alternate frame rates may be used for example, for implementing different readout rates.

It may however be possible to substantially shorten the time required for scanning the pixels and for transmitting the data. For example, by increasing the clock rate of the CMOS pixel array, it may be possible to reduce the time required to scan an individual frame to 3 microseconds or even less. Additionally, it may be possible to increase the data transmission rate of the transmitter 26 to even further shorten the overall time required for scanning the array pixels for transmitting the pixel data to the external receiver/recorder.

Therefore, variable frame rate in vivo imaging devices, as well as fixed frame rate devices, may be implemented which may be capable of frame rates of approximately 4-8 frames per second, and even higher.

When the method disclosed hereinabove for turning off the illuminating unit when the integrated output of the light sensing unit reaches a threshold value adapted to ensure a good average image quality is implemented, the tendency of the designer may be to operate the illuminating unit (such as, for example the illuminating unit 63 of FIG. 3) close to the maximal available light output capacity. This may be advantageous because of the shortened illumination period duration achievable which may improve image clarity by reducing movement induced image blurring.

It may not always be possible or desired to operate the illuminating unit close to the maximal possible light output capacity. Therefore, it may be desired to start the operation of the illuminating unit 63 at a given light output which is lower than the maximal light output of illuminating unit 63.

In a second illumination control method, the illuminating unit 63 of FIG. 3 may be initially operated at a first light output level at the beginning of each of the imaging cycles. The light sensing unit 67 may be used to measure the amount of light during a short illumination sampling period.

Figure 10A:
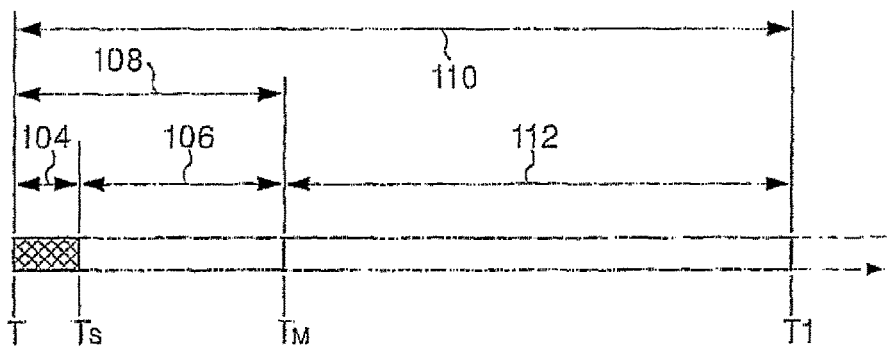
FIG. 10A is a timing diagram schematically illustrating an imaging cycle of an in vivo imaging device using an automatic illumination control method, in accordance with another embodiment of the present invention.
Figure 10B:
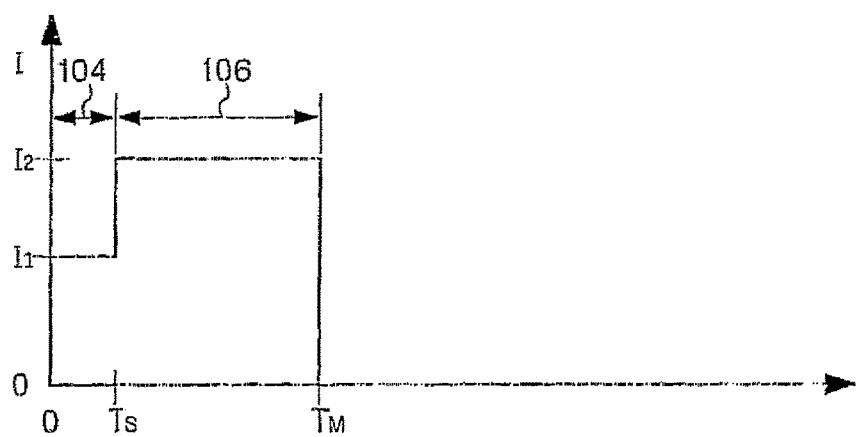
FIG. 10B is a schematic exemplary graph representing the light intensity as a function of time, possible when using a method of automatic illumination control, according to an embodiment of the invention, for example as illustrated in FIG. 10A.
Figure 10C:
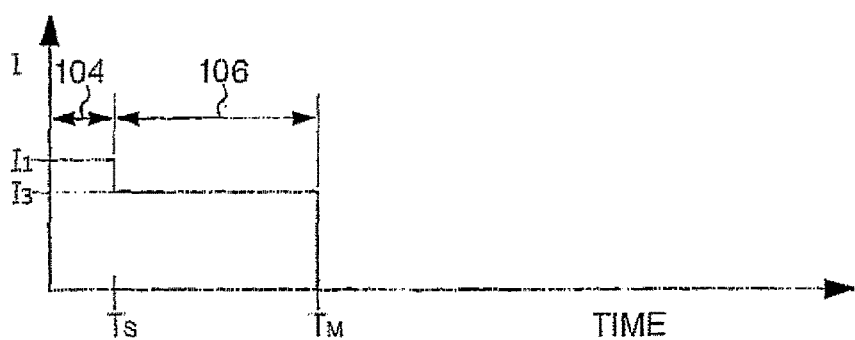
FIG. 10C is another exemplary schematic graph representing another example of the light intensity as a function of time, possible when using a method of automatic illumination control, according to an embodiment of the invention, illustrated in FIG. 10A.

Reference is now made to FIGS. 10A, 10B and 10C. FIG. 10A is a timing diagram schematically illustrating an imaging cycle of an in vivo imaging device using an automatic illumination control method in accordance with another embodiment of the present invention. FIG. 10B is an exemplary schematic graph representing an example of the light intensity as a function of time, possible when using the method of automatic illumination control illustrated in FIG. 10A. FIG. 10C is a schematic graph representing another example of the light intensity as a function of time, possible when using the method of automatic illumination control illustrated in FIG. 10A.

In FIGS. 10A, 10B and 10C, the horizontal axes of the graphs represents time in arbitrary units. In FIGS. 10B and 10C, the vertical axis represents the intensity I of the light output by the illuminating unit 63 (FIG. 3).

The automatic illumination control method illustrated in FIG. 10A operates by using an illumination sampling period 104 included in a total illumination period 108. An imaging cycle 110 includes the total illumination period 108 and a dark period 112. The illuminating unit 63 may illuminate the intestinal wall 76 within the duration total illumination period 108. The dark period 112 may be used for scanning the pixels of the CMOS imager 64 and for processing and transmitting the image data as disclosed in detail hereinabove.

The total illumination period of the imaging cycle starts at time T and ends at time $T_M$. The time $T_M$ is fixed with respect to the beginning time T of the imaging cycle 110, and represents the maximal allowable illumination time. Practically, the time $T_M$ may be selected to reduce the possibility of image blurring as explained hereinabove. For example, the time $T_M$ may be selected as 20 milliseconds from the time of beginning T of the imaging cycle 110 (in other words, the duration of the total illumination period 108 may be set at 30 milliseconds), but other larger or smaller values of the time $T_M$ and of the total illumination period 108 may also be used.

The total illumination period 108 may include an illumination sampling period 104 and a main illumination period 106. The illumination sampling period 104 starts at time T and ends at time $T_S$. The main illumination period 106 starts at time $T_S$ and ends at time $T_M$.

In an exemplary embodiment of the method, the duration of the illumination sampling period 104 may be set at approximately 2-5 milliseconds, but other larger or shorter duration values may be used depending, inter alia, on the type and characteristics of the light sensing unit 67, its sensitivity to light, its signal to noise ratio (S/N), the intensity $I_1$ at which the illuminating unit 63 is operated during the illumination sampling period 104, and other implementation and manufacturing considerations.

Turning to FIGS. 10B and 10C, during the illumination sampling period 104, the illuminating unit 63 is operated such that the intensity of light is $I_1$. The light sensing 67 may sense the light reflected from and diffused by the intestinal wall 76. The illumination control unit 40A may integrate the intensity signal to determine the quantity Q of light reaching the light sensing unit 67 within the duration of the illumination sampling period 104. The illumination control unit 40A may then compute from the value Q and from the known duration of the main illumination period 106, the intensity of light $I_N$ at which the illuminating unit 63 needs to be operated for the duration of the main illumination period 106 in order to provide adequate average exposure of the CMOS sensor 64. In one embodiment an estimated total amount of light received is kept substantially constant across a set of imaging cycles, or is kept within a certain target range. The computation may be performed, for example, by subtracting from a fixed light quantity which is desired to be received or applied the amount of light recorded during the sampling period 104 and dividing the result by a fixed time period which corresponds to the main illumination period 106. One possible way to perform the computation would be using equation 1 as follows:

$$I_N = (Q_T - Q)/\Delta T_{MAIN} \qquad \text{equation 1}$$

Wherein, $\Delta T_{MAIN}$ is the duration of the main illumination period 106, $Q_T$ is the total quantity of light that needs to reach the light sensing unit 67 within an imaging cycle to ensure adequate average exposure of the CMOS sensor 64, and Q is the quantity of light reaching the light sensing unit 67 within the duration of an illumination sampling period 104 of an imaging cycle.

It is noted that the value of $Q_T$ may be empirically determined.

FIG. 10B schematically illustrates a graph showing the intensity of light produced by the illuminating unit 63 as a function of time for an exemplary imaging cycle. During the illumination sampling period 104 the light intensity has a value $I_1$. After the end of the illumination sampling period 104, the light intensity $I_N = I_2$ may be computed as disclosed in equation 1 hereinabove, or by using any other suitable type of analog or digital computation.

For example, if the computation is digitally performed by the controller/processor 36 of FIG. 2, the value of $I_N$ may be computed within a very short time (such as for example less than a microsecond) compared to the duration of the main illumination period 106.

If the computation of $I_N$ is performed by an analog circuit (not shown) which may be included in the illumination control unit 40 of FIG. 2, or in the illumination control unit 40B of FIG. 6, or in the illumination control unit 40A of FIG. 3, the computation time may also be short compared to the duration of the main illumination period 106.

After the computation of $I_2$ for the imaging cycle represented in FIG. 10B is completed, the illumination control unit 40A may change the intensity of the light output of the illuminating unit of the imaging device to $I_2$. This may be achieved, for example, by increasing the amount of current output from the LED driver unit 84 of FIG. 7, or by increasing the amount of current output from one or more LED driver units (not shown in detail) which may be included in the illumination control unit 40A to supply current to the light sources 63A, 63B, 63C, and 63D. At the end of the main illumination period 108 (at time $T_M$), the illumination control unit 40A may switch the illuminating unit 63 off until time T1 which is the beginning of a new imaging cycle (not shown). At the beginning of the new imaging cycle, the light intensity is switched again to the value $I_1$ and a new illumination sampling period begins.

FIG. 10C schematically illustrates a graph showing the intensity of light produced by the illuminating unit 63 as a function of time for another different exemplary imaging cycle. The illumination intensity $I_1$ is used throughout the illumination sampling period 104 as disclosed hereinabove. In this imaging cycle, however, the value of Q measured for the illumination sampling period 104 is higher than the value of Q measured for the illumination sampling period of FIG. 10B. This may happen, for example, due to movement of the position of the imaging device 60 relative to the intestinal wall 76. Therefore the computed value of $I_3$ is lower than the value of $I_2$ of the imaging cycle illustrated in FIG. 10B. The value of $I_3$ is also lower than the value of $I_1$. Thus, the intensity of light emitted by the illuminating unit 63 during the main illuminating period 106 illustrated in FIG. 10C is lower than the intensity of light emitted by the illuminating unit 63 during the illumination sampling period 104 of FIG. 10C.

It is noted that if the computed value of $I_3$ is equal to the value of $I_1$ (case not shown in FIGS. 10B-10C) the illumination intensity may be maintained at the initial value of $I_1$ for the duration of the total illumination period 108, and no modification of the illumination intensity is performed at time $T_M$.

An advantage of the second illumination control method disclosed hereinabove may be that it may at least initially avoid the operating of the illuminating unit 63 at its maximal light output intensity. This may be useful for improving the performance of the power sources, such as, for example, the power source(s) 25 of FIG. 1, and may extend the useful operational life thereof. It is known in the art that many batteries and electrochemical cells do not perform optimally when they are operated near their maximal current output. When using the second illumination method, the light sources (such as the light sources 63A, 63B, 63C, and 63D of FIG. 3) are initially operated at a light intensity $I_1$ which may be a fraction of their maximal output light intensity. Thus, in cases where it is determined that the maximal light output intensity is not required for the current frame acquisition, the light sources may be operated at a second light intensity level (such as, for example the light intensity level $I_3$ which is lower than the light intensity level $I_1$). Thus, the second illumination control method may reduce the current required for operating the illuminating unit 63 drawn from the batteries or other power sources of the imaging device which may extend the useful operational life of the batteries or of other power sources used in the imaging device.

According to one embodiment a combination of both methods (variable duration and variable intensity) is possible.

It will be appreciated by those skilled in the art that the embodiments of the present invention are not limited to the use of a single light sensing element and/or a single light source. Additionally, it will be appreciated that the light sensing elements may include photo detectors that are separate from an imager, or are part of an imager.

Figure 11:
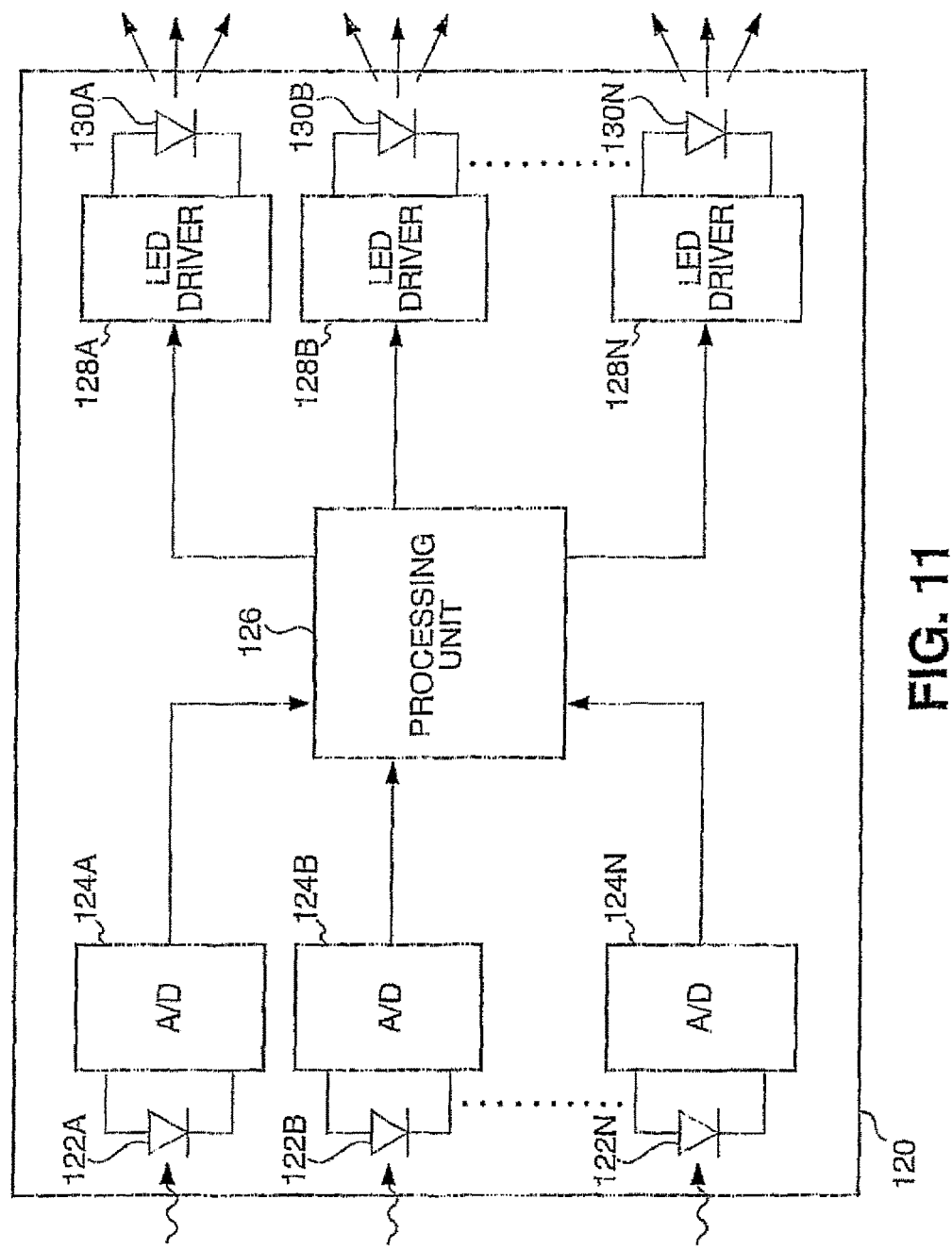
FIG. 11 is a schematic diagram illustrating an illumination control unit including a plurality of light sensing units for controlling a plurality of light sources, in accordance with an embodiment of the present invention.

Reference is now made to FIG. 11 which is a schematic diagram illustrating an illumination control unit for controlling a plurality of light sources, in accordance with an embodiment of the present invention.

The illumination control unit 120 includes a plurality of light sensing units 122A, 122B, . . . 122N, suitably interfaced with a plurality of analog to digital (A/D) converting units 124A, 124B, . . . 124N, respectively. The A/D converting units are suitably connected to a processing unit 126. The processing unit 126 is suitably connected to a plurality of LED drivers 128A, 128B, . . . 128N which are suitably connected to a plurality of LED light sources 130A, 130B, . . . 130N.

Signals representing the intensity of light sensed by the light sensing units 122A, 122B, . . . 122N are fed to the A/D converting units 124A, 124B, . . . 124N, respectively, which output digitized signals. The digitized signals may be received by the processing unit 126 which may process the signals. For example the processing unit 136 may perform integration of the signals to compute the quantity of light sensed by one or more of the light sensing units 122A, 122B, . . . 122N. The computed quantity of light may be the total combined quantity of light sensed by all the light sensing units 122A, 122B, . . . 122N taken together, or may be the individual quantities of light separately computed for each individual light sensing unit of the light sensing units 122A, 122B, . . . 122N.

The processing unit 136 may further process the computed light quantity or light quantities, to provide control signals to the LED drivers 128A, 128B, . . . 128N which in turn may provide, individually or in combination, suitable currents to the LED light sources 130A, 130B, . . . 130N. According to one embodiment of the present invention, each sensor may be directly related to one or more illumination sources.

According to some embodiments of the present invention, individual control of illumination sources may be enabled by using special control pixels. These control pixels may be adapted for fast read-out, which is well known in the art. A fast read-out procedure may not reset the pixel values.

It is noted that the illumination control unit 120 of FIG. 11 may be operated using different processing and control methods.

In accordance with one embodiment of the present invention, all the light sensing units 122A, 122B, . . . 122N may be used as a single light sensing element and the computation is performed using the combined total quantity of light to simultaneously control the operation of all the LED light sources 130A, 130B, . . . 130N together. In this embodiment, the illumination control unit 120 may be implemented using, for example, the first illumination control method as disclosed hereinabove and illustrated in FIGS. 5, 8, and 9, which uses a fixed illumination intensity and computes the termination time of the illumination. According to other embodiments multiple A/D units (e.g., 124) are not included, rather analog processing is performed.

Alternatively, in accordance with another embodiment of the present invention, the illumination control unit 120 may be implemented using the second illumination control method, for example, as disclosed hereinabove and illustrated in FIGS. 10A-10C which uses a first illumination intensity $I_1$ in an illumination sampling period and computes a second light intensity $I_N$ for use in a main illumination period as disclosed in detail hereinabove. In such a case, the illumination intensity $I_1$ used throughout the illumination sampling period 104 (see FIGS. 10A-10C) may be identical for all the LED light sources 130A, 130B, . . . 130N, and the illumination intensity $I_N$ used throughout the main illumination period 106 (FIGS. 10A-10C) may be identical for all the LED light sources 130A, 130B, . . . 130N.

In accordance with another embodiment of the present invention, each of the light sensing units 122A, 122B, . . . 122N may be used as a separate light sensing unit and the computation may be performed using the individual quantities of light sensed by each of the light sensing units 122A, 122B, . . . 122N to differentially control the operation of at least one of the LED light sources 130A, 130B, . . . 130N respectively or in any combination. In this embodiment, the illumination control unit 120 may be implemented using the first illumination control method as disclosed hereinabove and illustrated in FIGS. 5, 8, and 9, which uses a fixed illumination intensity for each of the LED light sources 130A, 130B, . . . 130N and may separately compute the termination time of the illumination for each of the LED light sources 130A, 130B, . . . 130N. In such a manner, sets of light sources 130A, 130B, . . . 130N (where a set may include one) may be paired with sets of sensors 122A, 122B, . . . 122N.

Alternatively, in accordance with another embodiment of the present invention, the illumination control unit 120 may be implemented using the second illumination control method as disclosed hereinabove and illustrated in FIGS. 10A-10C which uses a first illumination intensity $I_1$ in an illumination sampling period and computes a second light intensity $I_N$ for use in a main illumination period as disclosed in detail hereinabove. In such a case, the illumination intensity $I_1$ may be identical for all the LED light sources 130A, 130B, . . . 130N, and the illumination intensity $I_N$ may be identical for all the LED light sources 130A, 130B, . . . 130N.

Typically, this embodiment may be used in cases in which the positioning of the light sources 130A, 130B, . . . 130N and the light sensing units 122A, 122B, . . . 122N in the imaging device is configured to ensure that a reasonably efficient "local control" of illumination is enabled and that the cross-talk between different light sources is at a sufficiently low level to allow reasonable local control of the illumination intensity produced by a one or more of the light sources 130A, 130B, . . . 130N by processing the signals from one or more light sensing unit which are associated in a control loop with the one or more light sources.

Figure 12:
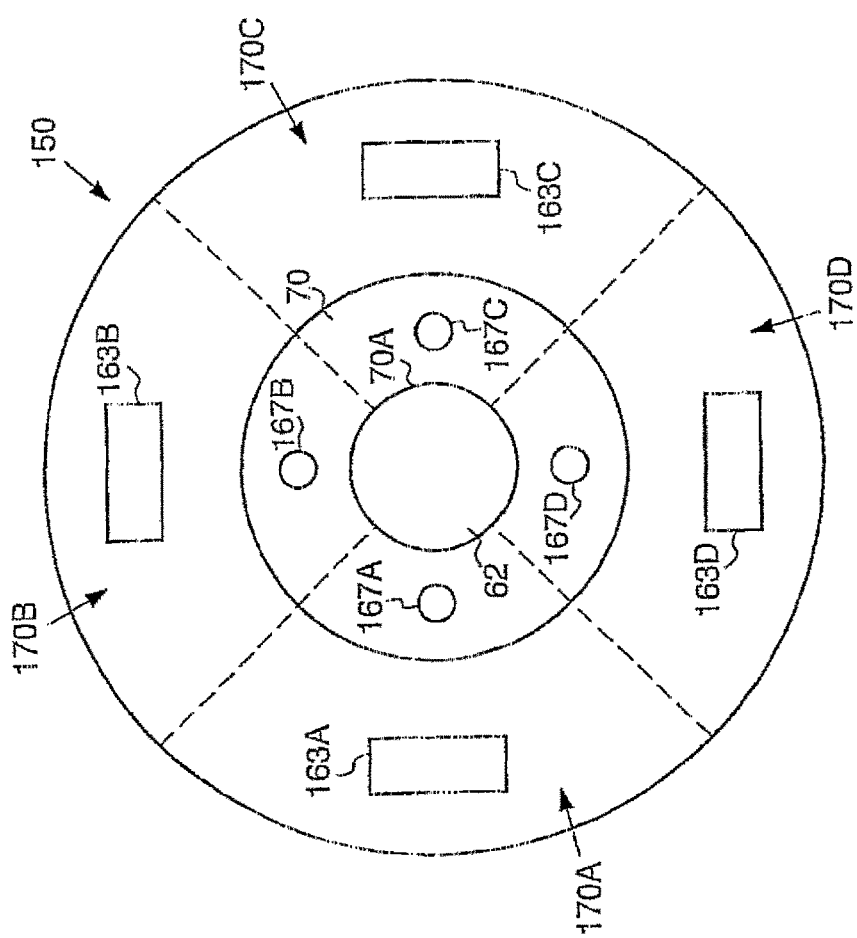
FIG. 12 is a schematic diagram illustrating a front view of an autonomous imaging device having four light sensing units and four light sources, in accordance with an embodiment of the present invention.

Reference is now made to FIG. 12 which is a schematic diagram illustrating a front view of an autonomous imaging device having four light sensing units and four light sources, in accordance with an embodiment of the present invention.

The device 150 includes four light sources 163A, 163B, 163C and 163D and four light sensing units 167A, 167B, 167C and 167D. The light sources 163A, 163B, 163C and 163D may be the white LED sources as disclosed hereinabove, or may be other suitable light sources. The light sensing units 167A, 167B, 167C and 167D are attached on the surface of the baffle 70, surrounding the aperture 62. The front part of the device 150 may include four quadrants 170A, 170B, 170C and 170D. The device 150 may include an illumination control unit (not shown in the front view of FIG. 12), and all the optical components, imaging components, electrical circuitry, and power source(s) for image processing and transmitting as disclosed in detail hereinabove and illustrated in the drawing Figures (See FIGS. 1, 2).

The quadrants are schematically represented by the areas 170A, 170B, 170C and 170D between the dashed lines. In accordance with an embodiment of the invention, the device 150 may include four independent local control loops. For example, the light source 163A and the light sensing unit 167A which are positioned within the quadrant 170A may be suitably coupled to the illumination control unit (not shown) in a way similar to the coupling of the light sources 38A-38N and the light sensing unit(s) 42 to the illumination control unit 40 of FIG. 2. The signal from the light sensing unit 167A may be used to control the illumination parameters of the light source 163A using any of the illumination control methods disclosed hereinabove, forming a local control loop for the quadrant 170A.

Similarly, the signal from the light sensing unit 167B may be used to control the illumination parameters of the light source 163B using any of the illumination control methods disclosed hereinabove, forming a local control loop for the quadrant 170B, the signal from the light sensing unit 167C may be used to control the illumination parameters of the light source 163C using any of the illumination control methods disclosed hereinabove, forming a local control loop for the quadrant 170C, and the signal from the light sensing unit 167D may be used to control the illumination parameters of the light source 163D using any of the illumination control methods disclosed hereinabove, forming a local control loop for the quadrant 170D.

It is noted that there may be some cross-talk or interdependency between the different local control loops, since practically, some of the light produced by the light source 163A may be reflected from or diffused by the intestinal wall and may reach the light sensing units 167B, 167C, and 167D which form part of the other local control loops for the other quadrants 170B, 170C, and 170D, respectively.

The arrangement of the positions light sensing units 167A, 167B, 167C and 167D and the light sources 163A, 163B, 163C and 163D within the device 150 may be designed to reduce such cross-talk.

In other embodiments of the invention it may be possible to use processing methods such as "fuzzy logic" methods or neural network implementations to link the operation of the different local control loops together. In such implementations, the different local control loops may be coupled together such that information from one of the light sensing unit may influence the control of illumination intensity of light sources in other local control loops.

It is noted that, while the imaging device 150 illustrated in FIG. 12 includes four light sources and four light sensing units, The number of light sources may vary and the imaging device of embodiments of the present invention may be constructed with a different number (higher or lower than four) of light sources. Similarly, the number of the light sensing units may also vary, and any suitable or practical number of light sensing units may be used. Additionally, it is noted that the number of light sensing units in a device need not be identical to the number of light sources included in the device. Thus, for example, a device may be constructed having three light sensing units and six light sources. Or in another example, a device may be constructed having ten light sensing units and nine light sources.

The factors determining the number of light sources and the number of light sensing units may include, inter alia, the geometrical (two dimensional and three dimensional) arrangement of the light sources and the light sensing units within the device and their arrangement relative to each other, the size and available power of the light sources, the size and sensitivity of the light sensing units, manufacturing and wiring considerations.

The number of local control loops may also be determined, inter alia, by the degree of uniformity of illumination desired, the degree of cross-talk between the different local control loops, the processing power of the illumination control unit available, and other manufacturing considerations.

The inventors of the present invention have noticed that it is also possible to achieve illumination control using one or more of the light sensitive pixels of the imager itself, instead of or in addition to using dedicated light sensing unit(s) which are not part of the imager. In addition, special light sensing elements may be integrated into the pixel array on the surface of the CMOS imager IC.

For example, in CMOS type imagers, some of the pixels of the CMOS imager may be used for controlling the illumination, or alternatively, specially manufactured light sensitive elements (such as, analog photodiodes, or the like) may be formed within the pixel array of the imager.

Figure 13:
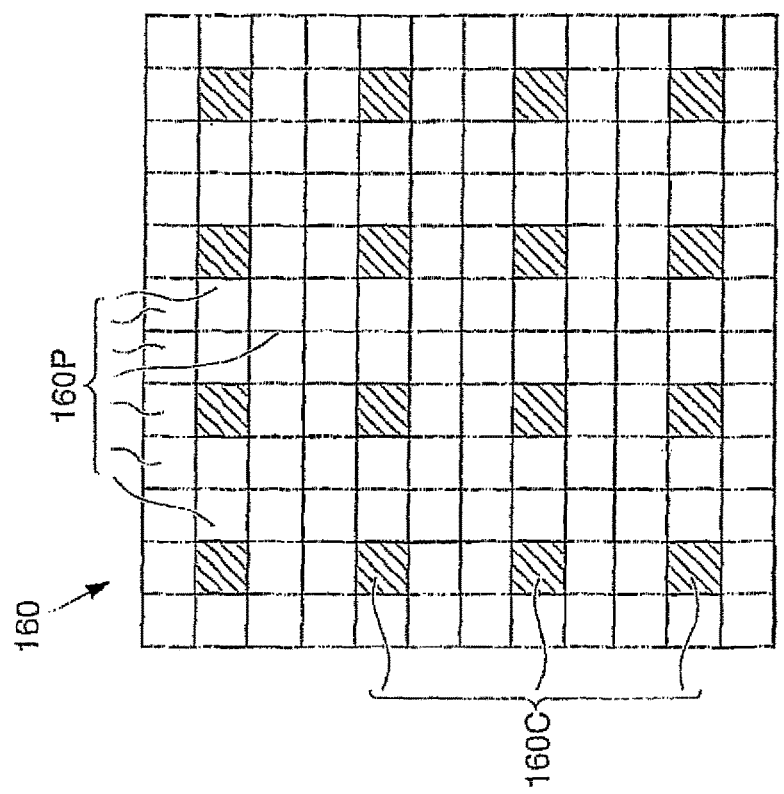
FIG. 13 is a schematic top view illustrating the arrangement of pixels on the surface of a CMOS imager usable for illumination control, in accordance with an embodiment of the present invention.

Reference is now made to FIG. 13 which is a top view schematically illustrating the arrangement of pixels on the surface of a CMOS imager usable for illumination control, in accordance with an embodiment of the present invention. It is noted that the pixel arrangement in FIG. 13 is only schematically illustrated and the actual physical arrangement of the circuitry on the imager is not shown.

The surface of the CMOS imager 160 is schematically represented by a 12×12 array comprising 144 square pixels. The regular pixels 160P are schematically represented by the white squares. The CMOS imager also includes sixteen control pixels 160C, which are schematically represented by the hashed squares.

It is noted that while the number of the pixels in the CMOS imager 160 was arbitrarily chosen as 144 for the sake of simplicity and clarity of illustration only, the number of pixels may be larger or smaller if desired. Typically, a larger numbers of pixels may be used to provide adequate image resolution. For example a 256×256 pixel array may be suitable for GI tract imaging.

In accordance with an embodiment of the present invention, the control pixels 160C may be regular CMOS imager pixels which are assigned to be operated as control pixels. In accordance with this embodiment, the control pixels 160C may be scanned at a different time than the regular imaging pixels 160P. This embodiment has the advantage that it may be implemented with a regular CMOS pixel array imager.

Turning back to FIG. 10A, the timing diagram of FIG. 10A may also be used, according to one embodiment, to illustrate the automatic illumination control method using control pixels. The method may operate by using a fast scan of the control pixels 160C at the beginning of each imaging cycle 110. The illuminating unit (not shown) may be turned on at the beginning of the imaging cycle 110 (at time T). The scanning of the control pixels 160C may be performed similar to the scanning of the regular pixels 160P, except that the scanning of all of the control pixels 160C occurs within the illumination sampling period 104. The control pixels 160C may be serially scanned within the duration of the illumination sampling period 104. This is possible due to the ability to randomly scan any desired pixel in a CMOS pixel array, by suitably addressing the pixel readout lines (not shown) as is known in the art.

It is noted that since the control pixels 160C are scanned serially (one after the other), the control pixel which is scanned first has been exposed to light for a shorter time period than the control pixels which are scanned next. Thus, each control pixel is scanned after it has been exposed to light for a different exposure time period.

If one assumes that the intensity of light reflected from the intestinal wall does not change significantly within the duration of the illumination sampling period 104, it may be possible to compensate for this incrementally increasing pixel exposure time by computationally correcting the average measured light intensity for all the control pixels 160C, or the computed average quantity of light reaching all the control pixels 160C. For example, a weighted average of the pixel intensities may be computed.

Alternatively, in accordance with another embodiment of the present invention, the illuminating unit 63 may be turned off after the end on the illumination sampling period 104 (the turning off is not shown in FIG. 10A). This turning off may enable the scanning of the control pixels 160C while the pixels 160C are not exposed to light and may thus prevent the above described incremental light exposure of the control pixels.

After the scanning (readout) of all the control pixels 160C is completed and the scanned control pixel signal values are processed (by analog or by digital computation or processing), the value of the required illumination intensity in the main illumination period may be computed, for example, by the illumination control unit 40A (or, for example, by the illumination control unit 40 of FIG. 2).

The computation of the required illumination intensity or of the current required from the LED driver unit 84 may be performed as disclosed hereinabove, using the known value of $I_1$ (see FIG. 10B) and may or may not take into account the duration of the period in which the illuminating unit 63 was turned off (this duration may be approximately known from the known time required to scan the control pixels 160C and from the approximate time required for the data processing and/or computations). The illumination unit 63 may then be turned on (the turning on is not shown in FIG. 10A for the sake of clarity of illustration) using the computed current value to generate the required illumination intensity value $I_2$ (see FIG. 10B) till the end of the main illumination period 106 at time $T_M$.

It is noted that if the number of control pixels 160C is small the time required for scanning the control pixels 160C may be short in comparison to the total duration of the total illumination period 108. For example, if the scan time for scanning a single control pixel is approximately 6 microseconds, the scanning of 16 control pixels may require about 96 microseconds. Since the time required for computing the required light intensity may also be small (a few microseconds or tens of microseconds may be required), the period of time during which the illumination unit 63 is turned off at the end of the illumination sampling period 104 may comprise a small fraction of the main illumination period 108 which may typically be 20-30 milliseconds.

It may also be possible to compute a weighted average in which the intensity read for each pixel may be differently weighted according to the position of the particular control pixel within the entire pixel array 160. Such weighting methods may be used for obtaining center biased intensity weighting, as is known in the art, or any other type of biased measurement known in the art, including but not limited to edge (or periphery) biased weighting, or any other suitable type of weighting known in the art. Such compensating or weighting computations may be performed by an illumination control unit (not shown) included in the imaging device, or by any suitable processing unit (not shown), or controller unit (not shown) included in the imaging device in which the CMOS imager 160 illustrated in FIG. 13 is included.

Thus, if an averaging or weighting computation is used, after the readout of the control pixels and any type of compensation or weighting computation is finished, the illumination control unit (not shown) may compute the value of the weighted (and/or compensated) quantity of light sensed by the control pixels 160C and use this value for computing the value of $I_2$.

It is noted that the ratio of the number of the control pixels 160C to the regular pixels 160P should be a small number. The ratio of 16/144 which is illustrated is given by example only (for the sake of clarity of illustration). In other implementations the ratio may be different depending, inter alia, on the total number of pixels in the CMOS array of the imager and on the number of control pixels used. For example in a typical 256×256 CMOS pixel array it may be practical to use 16-128 pixels as illumination control pixels for illumination control purposes. The number of control pixels in the 256×256 CMOS pixel array may however also be smaller than 16 control pixels or larger than 128 control pixels.

Generally, the number of control pixels and the ratio of control pixels to regular pixels may depend, inter alia, on the total number of pixels available on the imager pixel array, on the pixel scanning speed of the particular imager, on the number of control pixels which may be practically scanned in the time allocated for scanning, and on the duration of the illumination sampling period.

An advantage of the embodiments using automatic illumination control methods in which some of the pixels of the CMOS imager pixel array (such as for example the example illustrated in FIG. 13) is that in contrast to light sensitive sensors which may be disposed externally to the surface of the imager (such as for example, the light sensing unit 67 of FIG. 3), the control pixels 160C actually sense the amount of light reaching the imager's surface since they are also imaging pixels disposed on the surface of the imager. This may be advantageous due to, inter alia, higher accuracy of light sensing, and may also eliminate the need for accurately disposing or the light sensing unit at an optimal place in the optical system, additionally, the control pixels may have signal to noise characteristics and temperature dependence properties similar to the other (non-control) pixels of the imager.

Another advantage of using control pixels is that no external light sensing units are needed which may reduce the cost and simplify the assembly of the imaging device.

It is noted that, according to one embodiment, in a CMOS imager such as imager 160, the scanning of the control pixels 160C after the illumination sampling period 104 does not reset the pixels. Thus, the control pixels 160C continue to sense and integrate the light during the main illumination period 106, and are scanned after the time $T_M$ together with all the other regular pixels 160P of the imager 160. Thus, the acquired image includes the full pixel information since the control pixels 160C and the regular pixels 160P have been exposed to light for the same duration. The image quality or resolution is thus not significantly affected by the use of the control pixels 160C for controlling the illumination.

It is also noted that while the arrangement of the control pixels 160C on the imager 160 is symmetrical with respect to the center of the imager, any other suitable arrangement of the pixels may be used. The number and the distribution of the control pixels on the imager 160 may be changed or adapted in accordance with the type of averaging used and/or for example, with the type of acquired images.

Furthermore, the control pixels may be grouped into groups that may be processed separately to allow local illumination control in imagers using a plurality of separately controllable light sources.

Figure 14:
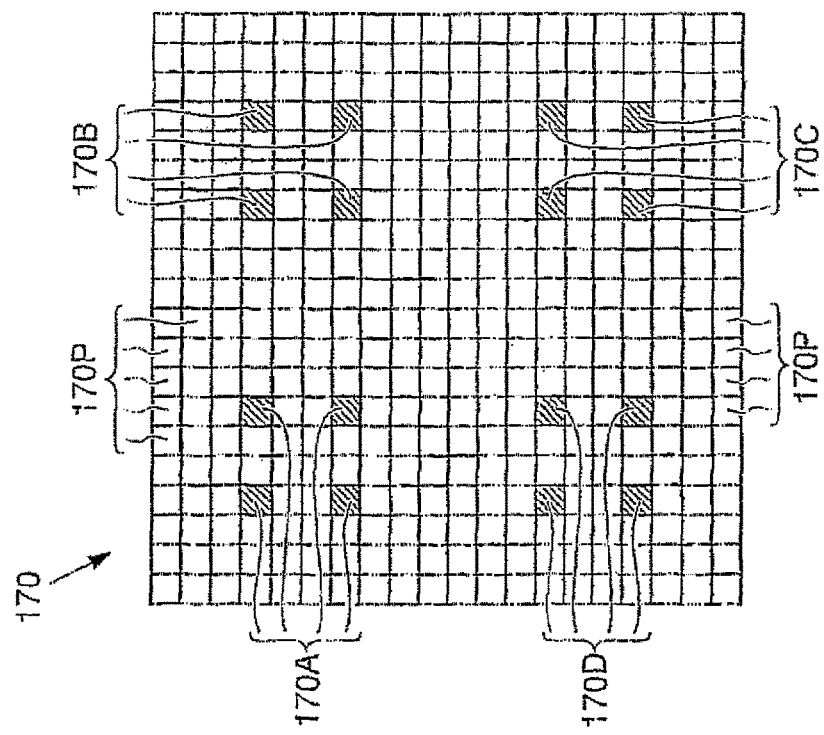
FIG. 14 is a schematic top view of the pixels of a CMOS imager illustrating an exemplary distribution of control pixel groups suitable for being used in local illumination control in an imaging device, according to an embodiment of the invention.

Reference is now made to FIG. 14, which is a schematic top view of the pixels of a CMOS imager illustrating an exemplary distribution of control pixel groups suitable for being used in local illumination control in an imaging device, in accordance with an embodiment of the present invention.

The illustrated imager 170 is a 20×20 pixel array having 400 pixels. The control pixels are schematically represented by the hashed squares 170A, 170B, 170C and 170D and the remaining imager pixels are schematically represented by the non-hashed squares 170P. Four groups of control pixels are illustrated on the imager 170.

The first pixel group includes four control pixels 170A arranged within the top left quadrant of the surface of the imager 170. The second pixel group includes four control pixels 170B arranged within the top right quadrant of the surface of the imager 170. The third pixel group includes four control pixels 170C arranged within the bottom right quadrant of the surface of the imager 170. The fourth pixel group includes four control pixels 170D arranged within the top left bottom quadrant of the surface of the imager 170.

If the imager 170 is disposed in an autonomous imaging device having a plurality of light sources (such as, but not limited to the device 150 of FIG. 12), each of the four groups of control pixels 170A, 170B, 170C and 170D may be scanned and processed as disclosed hereinabove to provide data for locally controlling the illumination level reaching each of the respective four quadrants of the imager 170. The scanned data for each of the pixels within each of the four groups may be processed to compute a desired value of illumination intensity for the respective imager quadrant. The methods for controlling the illumination using separate local control loops may be similar to any of the methods disclosed hereinabove with respect to the device 150 of FIG. 12, except that in the device 150 the light sensing units are units external to the imager and in the device 170, the control pixels used for sensing are imager pixels which are integral parts of the imager 170.

The illumination control methods using control pixels may implemented using the closed-loop method of terminating the illumination when the integrated sensor signal reaches a threshold level as disclosed hereinabove or may be implemented by using an initial illumination intensity in a sampling illumination period and adapting or modifying the illumination intensity (if necessary) in accordance with a value computed or determined from the control pixel scanning as disclosed hereinabove.

The signals or data of (representing the pixel charge) the pixel groups may be processed using averaging or weighted averaging methods to perform center biased or periphery biased averages or according to any other averaging or processing method known in the art. The results of the processing may be used as disclosed hereinabove to control the light sources (such as for example four light sources disposed within the imaging device in an arrangement similar to the arrangement of the four light sources 163A, 163B, 163C, and 163D of FIG. 12).

It will be appreciated by those skilled in the art that the number of control pixels and the distribution of the control pixels on the surface of the imager may be varied, inter alia, in accordance with the desired type of averaging, the required number of local illumination control groups, the number and position of the light sources available in the imaging device, the computational power available to the processing unit available, the speed of the illumination control unit, and other design considerations.

In accordance with another embodiment of the present invention, the control pixels 160C of FIG. 13 may be specially fabricated pixels, which are constructed differently than the regular pixels 160P. In accordance with this embodiment, the control pixels 160C may be fabricated as analog photodiodes with appropriate readout or sampling circuitry (not shown) as is known in the art. This implementation may use a specially fabricated custom CMOS imager in which the analog photodiodes serving as the control pixels 160C may be read simultaneously which may be advantageous since the readout or scanning time may be shorter than the time required to sequentially scan the same number of control pixels implemented in a regular CMOS pixel array having uniform pixel construction.

It is noted that when analog photodiodes or other known types of dedicated sensors are integrated into the CMOS pixel array of the imaging device, the acquired image will have "missing" image pixels, since the area in which the analog photodiode is disposed is not scanned together with the regular CMOS array pixels. The image data will therefore have "missing pixels". If, however, a small number of analog photodiodes or other dedicated control pixels is included in the CMOS pixel array, the missing pixels may not cause a significant degradation of image quality. Additionally, such dedicated analog photodiodes or other control pixels may be distributed within the pixel array and may be sufficiently spaced apart from each other, so that image quality may be only slightly affected by the missing image pixels.

It is noted that while the illumination control methods are disclosed for use in an autonomous imaging device such as the device 10A of FIG. 1, these illumination control methods may also be used with or without adaptations in other in-vivo imaging devices having an imager and an illumination unit, such as in endoscopes or catheter-like devices having imaging sensor arrays, or in devices for performing in-vivo imaging which are insertable through a working channel of an endoscope, or the like.

Additionally, the illumination control methods disclosed herein may be used in still cameras and in video cameras which include a suitable imager, such as a CMOS imager, and which include or are operatively connected to an illumination source.

Additionally, the use of control pixels implemented in a CMOS pixel array imagers, using selected regular pixels as control pixels or using specially fabricated control pixels such as the analog photodiodes or the like, may be applied for controlling the illumination of a flash unit or another illumination unit which may be integrated within the camera or may be external to the camera and operatively connected thereto.

The advantages of using control pixels which are part of the CMOS imager of the camera may include, inter alia, simplicity of construction and operation, the ability to implement and use a plurality of controllably interchangeable averaging methods including weighted averaging methods and biasing methods, as disclosed in detail hereinabove, increased accuracy of illumination control.

Additionally, in specialty cameras operating under conditions in which the light source included in the camera or operatively connected thereto is the only source of available illumination (such as, for example, in camera's operated at the bottom of the ocean, or in cameras which are designed to perform surveillance or monitoring in difficult to access areas which are normally dark), the use of illumination control methods disclosed hereinabove may allow to use shutterless cameras, which may advantageously increase the reliability of such devices, reduce their cost, and simplify their construction and operation.

It is noted that, while in the embodiments of the invention disclosed hereinabove the number and the arrangement of the control pixels are fixed, in accordance with another different embodiment of the present invention, the number and/or the geometrical configuration (arrangement) of the control pixels may be dynamically changed or controlled. For example, briefly turning to FIG. 2, the light sensing unit(s) 42 may represent one or more control pixels of a CMOS pixel array, and the illumination control unit 40, and/or the controller/processor unit 36 may be configured for changing the number of the control pixels used in an imaging acquisition cycle and/or for changing the arrangement of the control pixels on the pixel array of the imaging unit 32.

Such changing of control pixel number and/or arrangement may be performed, in a non-limiting example, by changing number and/or arrangement of the pixels selected to be scanned as control pixels during the illumination sampling period 104 (FIG. 10A). Such a changing may allow the use of different averaging arrangements and methods and may allow changing of different biasing methods for different imaging cycles.

Additionally, using dynamically controllable control pixel configuration, it may be possible to implement two or more illumination sampling periods within a single imaging cycle and to use a different pixel number or configuration for each of these two or more illumination sampling periods.

It may also be possible to remotely control the number and/or configuration of the control pixels, by instructions which are wirelessly transmitted to the telemetry unit, for example, telemetry unit 34 (FIG. 2), in which case the telemetry unit may be configured as a transceiver unit capable of transmitting data and of receiving control data transmitted to it by an external transmitter unit (not shown in FIG. 2).

It is noted that, while the embodiments disclosed hereinabove were based on modifying the light output from the illumination unit(s) (such as, for example the illumination unit 63 of FIG. 3) based on measurement and processing of the amount of light reaching the light sensing elements (such as, for example the light sensing unit 67 of FIG. 3, or the light sensing units 42 of FIG. 2, or the control pixels 160C of FIG. 13), another approach may be used.

According to some embodiments of the present invention, the gain of the pixel amplifiers of the imager (for example, imaging unit 32 of FIG. 2) and/or other parameters may be changed. The parameter change decisions may be based on, for example, the results of the measurement of the amount of light reaching the light sensing unit or units (such as, for example, the light sensing unit 42 of FIG. 2, the control pixels 160C of FIG. 13, or the like). In such an embodiment, the illumination unit of the imaging device(s) (such as, for example, the illumination unit 63A of FIG. 3, or the illumination unit 38 of FIG. 2 etc.) may be operated at a fixed or variable illumination intensity, for a fixed or variable time period. The light that reaches the light sensing unit(s) or the control pixels of the imaging device during a sampling period (e.g., a portion of the exposure period within a frame) may be measured at a sampling instance or point. A sampling instance or point may be a discrete point in time or may extend over a certain amount of time. Parameters such as the gain level or sensitivity of the imager pixel amplifiers, the light intensity, duration of illumination or other parameters may be changed individually or in any combination in relation to, for example, measurements of relative light saturation of selected pixels, to achieve proper or appropriate imaging.

For example, if the amount of light reaching the light sensing unit(s) during an illumination sampling period, as measured at at least one selected sampling instance (period), is approximately sufficient to ensure proper image exposure (relative to, for example, an expected threshold for a determined number of pixels), the exposure may be stopped. In this case full exposure has already been achieved, and no further exposure is necessary. In this case, no change is the current image gain level should be required when transmitting the image. In addition, since the exposure was relatively short, there should be no problem with blurring, which may accompany images recorded with long light exposures.

In the case where the measurement at a sampling instance determines that too little saturation has been attained (relative to a threshold value) during an illumination sampling period, the exposure should be continued to enable sufficient lighting for an image. However, too much exposure may cause blurring, so the imager may be commanded to lower the saturation threshold so as to have a shorter exposure. In addition to lowering the saturation threshold, in order to compensate for the short exposure, the imager may be commanded to provide a higher gain level for the image transmission, to enable enough exposure in spite of the short exposure time. For example, if the saturation threshold was halved to shorten the exposure sufficiently, the gain level will correspondingly need to be doubled to enable adequate exposure.

If too much light, possibly relative to an expected threshold, reaches the light sensing unit(s) during an illumination sampling period, the exposure may be stopped, and the pixel amplifier gain (or other parameters) may be decreased to prevent overexposure. Additional sampling periods may be instituted at chosen instances, to enable further fine-tuning of variables such as image gain and exposure time.

In addition to changes in the analog gain, which may be based on continuously scanning the analog output of a selected number of pixels during the early phase of the exposure period, the exposure may be stopped at any stage where full (e.g., adequate) saturation has been reached. In this way, for example, full image exposure may be provided in many cases of low exposure, by, for example, adding gain levels to images. In addition, over exposure can be prevented in many cases where there is high exposure, by, for example stopping exposure when saturation is attained. These changes may result in increased image quality, energy saving and/or other benefits.

Various embodiments may utilize various time, saturation, and voltage levels, and are not limited to the following defined levels. According to a particular application of the present embodiment, required time resolution, which defines the maximum read out time required to achieve saturation for all pre-selected pixels may be, for example, 0.25 s. Other values or ranges may be used.

According to some embodiments of the present invention, a total exposure time (e.g., an expected time required for adequate and/or correct exposure) may be defined (T1), within which an exposure measurement time (sampling time, such as $T1/_4$ or other times which are a portion of T1) may be defined. The discrete time instances, where changes of reference levels may occur and gain decisions may be taken, may be determined by T1. This value may be used indirectly to set time intervals such as $T1/_2$ and $T1/_4$, or other intervals, which may be sample time intervals for measuring pixel saturation. A maximum exposure time may also be defined ($T_M$). Typically, T1 and $T_M$ are both programmable. Typically, $T_M$ does not impact on the calculations, other than to set a maximal exposure time at which point exposure may be stopped, regardless of whether exposure saturation thresholds have been crossed. T1, on the other hand, may be used as the target exposure time. For example, T1 may refer to the expected exposure for adequate or complete saturation etc. At intervals $T1/_4$ and $T1/_2$, for example, the current system or method according to some embodiments sets the saturation threshold levels expected to be crossed before T1.

Typically, the device 30 transmits image information in discrete portions. Each portion typically corresponds to an image or frame. Other transmission methods are possible. For example, the device 30 may capture an image once every half second, and, after capturing such an image, transmit the image to the receiving antenna. Other capture rates are possible. Typically, the image data recorded and transmitted is digital color image data, although in alternate embodiments other image formats (e.g., black and white image data) may be used. In one embodiment, each frame of image data includes 256 rows of 256 pixels each, each pixel including data for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by, for example, a one byte (i.e., 0-255) brightness value. Other data formats may be used.

According to one embodiment, a reliable exposure measurement may require inclusion of every $n^{th}$ (e.g., $4^{th}$) pixel (which may be, for example, every second RED pixel, since there are typically more red pixels according to one embodiment, in every m lines (e.g. 10 out of 256 lines, in a typical approximately 66,000 pixel frame (e.g., 256×256 pixels)). This is equivalent to approximately 640 pixels in a typical frame. In one embodiment a reliable exposure measurement may require approximately 1.5% (for example, 11 pixels out of 640) of the selected pixels to be saturated in order to pass a saturation threshold, according to which gain decisions may be taken. Other frame sizes, percentages, and sample rates may be used, as appropriate. For example, 9, 11, 15, 24, and any other number of pixels can be used per frame or per sampled subset to determine a saturation threshold. Other individual pixels, e.g., non-red pixels, may be sampled, and sampling need not be based on color.

According to one embodiment, exposure time may be determined in, for example, 8 steps, from 5 ms to 40 ms. Other numbers of steps and intervals may be used, and intervals need not be used—e.g., exposure time may be determined on a continual basis. Furthermore, T1 may be digitally programmable, for example, in 8 steps with a, for example, logarithmic scale from, for example, 1 ms to 100 ms. According to one embodiment, the accuracy of detection levels may be defined, for example, as less than 5%. Other accuracy levels may be used, as appropriate.

The measurement of the exposure, according to one embodiment, may be performed on a subset of the pixels in the sensor array or imager. A determination as to whether a gain exposure change may be in order may be based on, for example, a percentage of the selected pixels that are saturated with light, relative to, for example, a saturation threshold for one or more pixels. The gain or other parameter setting decision may be based on one or more discrete time intervals within which the outputs from a nominal number of the selected number of pixels (e.g., 11 according to one embodiment) have reached a certain saturation level (e.g., reference level), or threshold. In this way, the exposure may continue until it is determined that the pixel output from the nominal number of pixels has reached a new saturation level, at which time the gain (or other parameter) level may be changed. According to one embodiment, exposure may continue until, for example, full saturation or maximum exposure time ($T_m$) is reached. It should be noted that determination of full saturation may differ according to the various gain (or other parameter) levels. For example, expected saturation at gain 1 may be V1, and expected saturation at gain 4 may be $V1/_4$. The reference voltage (Vref), or threshold voltage, for determining whether gain and/or exposure need to be changed may be defined at any discreet time interval, relative to the proportion of time to T1. For example, Vref may be equal to $Vfs/_4$ at time $T1/_4$, when the light reflection may initially be measured. Similarly, Vref may be equal to $Vfs/_2$ at time $T1/_2$, when the light reflection may subsequently be measured.

According to some embodiments of the present invention, an aggregate gray scale for the selected pixels (640 in the current example, etc.) may be measured at one or more intervals. The average may be compared to a saturation threshold, and gain decisions that are taken may be related to the average gray scale measurement and the relevant saturation threshold.

According to some embodiments of the present invention, the signal saturation level may be defined as Voltage Saturation, or Vsat, which represents a low pixel voltage, and may be defined as the pixel saturation referred to ground. Pixel reset level may be defined as Vrst, which represents the highest pixel voltage. Finally, Vfs may be defined as the A/D full-scale voltage, which represents the actual saturation or voltage level at a determined interval. Accordingly, Vsat=Vrst−Vsat=Vfs. In other words, the pixel signal level may be defined as the difference between the pixel reset level and the instantaneous pixel voltage, and may be a positive voltage, increasing from 0, during exposure. This "delta-voltage" may be compared with the comparator reference voltage, such as, for example $Vfs/_4$, at $T1/_4$.

Figure 15:
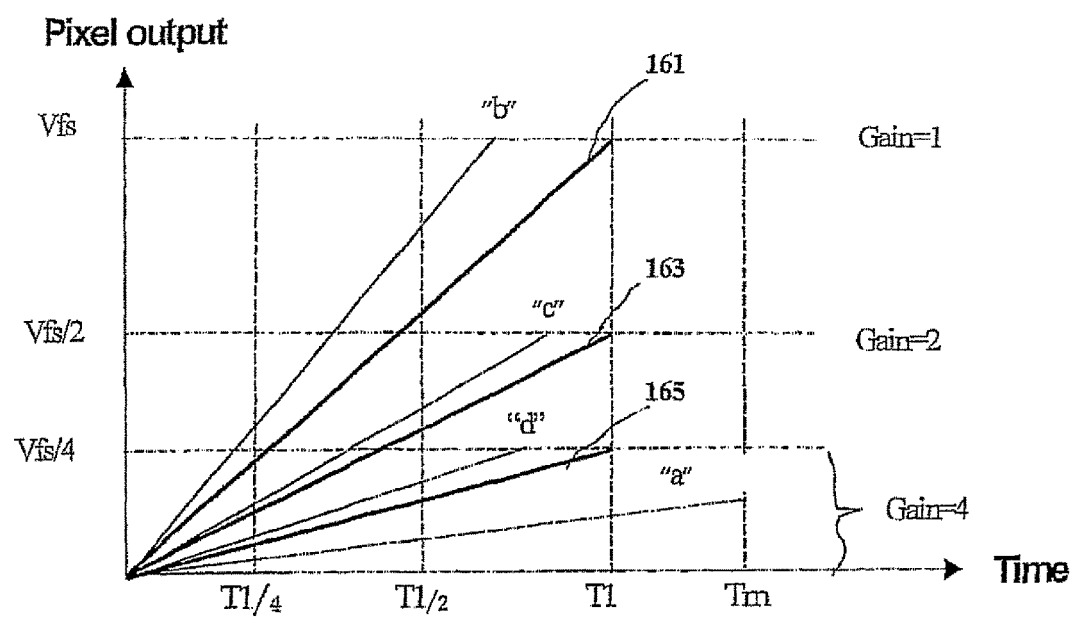
FIG. 15 is a schematic exemplary graph representing the light saturation as a function of pixel output and time, possibly when implementing light control, according to an embodiment of the invention.

Reference is now made to FIG. 15, which illustrates, according to one embodiment of the present invention, gain setting decisions that may be made, during an exposure period, as a function of pixel output (light saturation) vs. time. As can be seen in FIG. 15, for example, three gain settings that may be used are gain 1, gain 2 and gain 4. The thicker lines 161, 163 and 165 represent the gain limits or thresholds. The settings of FIG. 15 are provided as an example only, and are not meant to be limiting. Other numbers of gain settings may be used.

At an interval such as $T1/_4$, the saturation threshold (level) for selected pixels may be measured. The saturation threshold may be at, below, or above an expected threshold 161. In case "b", where the pixel output (average saturation of the selected pixels) is above the expected threshold 161, it is to be expected that full exposure will be completed within, for example, T1. Therefore no increase in gain, or sensitivity, is necessary, and exposure continues until full saturation (Vfs) is reached, at which time exposure is stopped.

In case "c", where the pixel output is below the expected threshold 161, but above a middle threshold 163, it is to be expected that exposure will not be completed within T1. Even though saturation may eventually be attained, the exposure will inevitably be longer than T1, which may cause a blurring effect. Therefore the imager may be commanded to increase the gain level from gain 1 to gain 2. Accordingly, the saturation threshold may be decreased by, for example, half, to Vfs/$_2$, which together with, for example, gain 2 amplification may provide full image exposure. The exposure may then continue until saturation level Vfs/$_2$ is reached, at which time exposure may be stopped. Vfs/$_2$ represents full saturation in this case since gain level 2 was applied. Other gain levels may be used.

In case "d" where the pixel output is below the middle threshold 163, but above a lower threshold 165, it may be expected that exposure will not be completed within T1. Therefore exposure continues and, in addition, a more significant increase in gain level may be necessary. The imager may be commanded to increase the gain level to gain 4, for example, and exposure may subsequently continue until corresponding saturation level Vfs/$_4$ is reached, at which time exposure may be stopped.

In case "a" where the pixel output is below the lower threshold 164, it may be expected that exposure will not be completed within T1, or even within T$_M$. Therefore an increase in gain level to gain 4, for example, may be necessary, and exposure may continue until T1. In this example, since full exposure has not been achieved even at T1, exposure may continue until T$_M$, to increase the possibility of sufficient exposure. T$_M$ may be the maximum exposure time for all cases.

As can been in the above example, and in relation to FIG. 15, full exposure has been achieved in 3 out of the 4 frames, and exposure time has likewise been reduced in 3 out of the four frames, possibly leading to significant increases in exposure clarity and decreases in usage of power resources. In alternate embodiments, other levels of alteration or improvement may result.

Additional measurement instances may also be provided, such as, for example, T1/2 and T1/$_3$ etc. The pixel exposures in the above scenarios may likewise be measured at this second interval, to establish whether further gain level changes are necessary.

In one embodiment, a first scan may be utilized to search for "white spots", or "hot spots", which are problematic (poorly or non-functioning) image receivers that may not be counted in the group of saturated pixels. This first scan may therefore be designed to detect, define and discard the problematic or non-functional pixels from the selected pixel group. Such a defective/non-functioning scan need not be used.

Following is an example of a non-limiting description of "pseudo-code", which may be used to implement an embodiment of the present invention. Other embodiments of the present invention may be implemented without coding, such as by using circuit design. Various embodiments of the present invention may be implemented using different code sequences and programming or logic design techniques:

```
Vref=Vfs/4
Gain=4
Exposure='on'
White_spots=Scan result
While Exposure='on'
    Pix_above_ref=Scan result %%%%For each scan
    If(t>=Tm)
        Exposure='off'
    Else %(t<Tm)
        If (Pix_above_ref-White_spots>='table_value')
            If (Gain=4)
                If (t<T1/4)
```

-continued

```
                    Vref=Vfs;
                    Gain=1;
                Else %(t>=T1/4)
                    If (t<T1/2)
                        Vref=Vfs/2;
                        Gain=2
                    Else % (t>=T1/2)
                        exposure='off'
                    End %(t<T1/2)
                End %(t<T1/4)
            Else %(Gain !=4)
                Exposure='off'
            End %(Gain=4)
        End % (Pix_above_ref-White_spots>='table_value')
    End %(t<Tm)
End %( While Exposure='on')
```

It is noted that such automatic gain control may result, under certain conditions in changes in the signal to noise ratio (S/N) of the imager in some cases. For example, increasing the pixel amplifier gain in CMOS pixel array imagers may result in higher S/N ratios, while increasing the exposure time (Tm) may increase the image "blur".

According to some embodiments of the present invention, the above described principles and related FIG. 15 may likewise be used to describe implementations of the present invention for other parameters such as illumination intensity and duty cycle etc., or in combination with such other parameters. For example, a method may be followed for determining light saturation in relation to light intensity and duty cycle etc., according to threshold values, at selected instances. These calculations of saturation level may determine whether such parameters are at, below or above a given threshold. Such a determination may enable decision making such as to change light illumination, duty cycle etc. to reflect the exposure needs of the relevant frames.

For example, the controller or any other element may measure light saturation levels in one or more light measuring elements, and in response to resulting measurements, may simultaneously at least one of control illumination duration, illumination intensity and/or image gain level. According to one embodiment of the present invention, illumination (exposure) may be increased eight-fold, for example, using the following or other possibilities:

a. duration×2, intensity×2, gain×2
b. duration×8, intensity×1, gain×1
c. duration×1, intensity×8, gain×1
d. duration×1, intensity×1, gain×8
e. duration×1.5, intensity×1.5, gain×3.56 etc.

Any other combinations of parameters that may be required to implement the above or alternate illumination targets may be utilized. Additional, any other suitable parameters may be factored in to the above described embodiments, individually or in any combination, to enable an in-vivo imaging device to provide more accurate exposure.

According to some embodiments of the present invention, a method is provided for determining the location or position of an in vivo device, such as an in vivo imaging capsule. For example, a method is provided for determining when an in vivo device enters into a body or enters into a particular area of the body, etc. This determination may be used for decision making, such as, for example, a decision whether an in vivo capsule should enter or exit an operational mode such as "fast mode", "slow mode", "standard mode" etc. A fast mode, for example, may enable the imaging device to attain an increased frame rate, which may be particularly useful for enabling rapid imaging of the esophagus after swallowing an imaging capsule. Such rapid imaging is not required, however, when the device is in, for example, the small intestine, therefore the device may be programmed to switch to a "standard mode" after a time period following the internalization of the device. Other operational mode changes may be effected. Thus, for example, the imaging device may send compressed data in "fast mode" when traveling down the esophagus, and then operate in regular uncompressed mode at a lower frame rate thereafter, when such a fast frame rate is not required.

In one embodiment of the invention, this may be accomplished by setting a mode, such as a fast mode, to end when a significant change has been determined in the environment surrounding the device. This may be accomplished by providing an environmental monitoring tool, such as a pH indicator, temperature gauge or light level indicator etc. in, on or outside of the imaging device to measure or otherwise determine environmental data. The monitoring or measurement tool may compare the measured data with previously measured environmental data to determine environmental changes. When, for example, the environment of the capsule has fallen below a certain pH level, this change in pH level may indicate that the esophagus has been traversed and that the imaging device is in the stomach. Various environments or environmental changes may be determined, depending on the measurement tools being used, such as outside the body, inside the body, in the mouth, in the throat, in the esophagus, in the stomach, in the small intestine etc.

In other embodiments, a mode, such as a fast mode, may be set to end a fixed amount of time, e.g. five minutes, after a change is detected. A change may be, for example, the capsule entering a dark environment such as the mouth. For example, a controller may configure a light source to provide a "dark frame" at determined frame intervals, such as, for example, at 1 frame out of every 256. During a dark frame, LEDs or other illumination sources may not be lit or may be lit for a brief instant, substantially inadequate to provide viable exposure for an image. For example, an in vivo imaging device may require a 25 ms exposure at a fixed light intensity to adequately light an internal lumen, yet purposefully provides an inadequate exposure of, for example, 5 ms. The device may periodically process the "dark" frame, which may be analyzed to determine the presence of ambient light in the environment of the device. If the ambient light is above a threshold level, indicating that there is a substantial amount of surrounding light and that a non-substantial amount of additional light is required for the image to attain saturation, it may be assumed that the capsule has not yet entered the body and that the fast mode should continue. If the ambient light during the dark frame is below a threshold level, indicating that the image requires a substantially significant amount of additional light to attain saturation, it may be assumed that the capsule has entered a darker environment, such as the body. In this case it may be assumed that the fast mode will no longer be necessary after a predetermined period of time, e.g., five minutes, by which time it may be assumed that the capsule has passed through the esophagus.

According to some embodiments, the exposure of the dark frame may be measured in relation to a light saturation threshold for the dark frames, to determine whether and/or by how much a change in an imager gain level is required. If the dark frame requires a substantially non-maximal gain factor, indicating that the image has a relatively adequate amount of light and only a relatively small gain level may be required to reach full exposure, the device may be defined as being outside a body. When the dark frame requires a large or maximal gain factor, indicating that a substantial gain is required for possibly reaching full saturation, the device may be defined as being inside a body.

Figure 16:
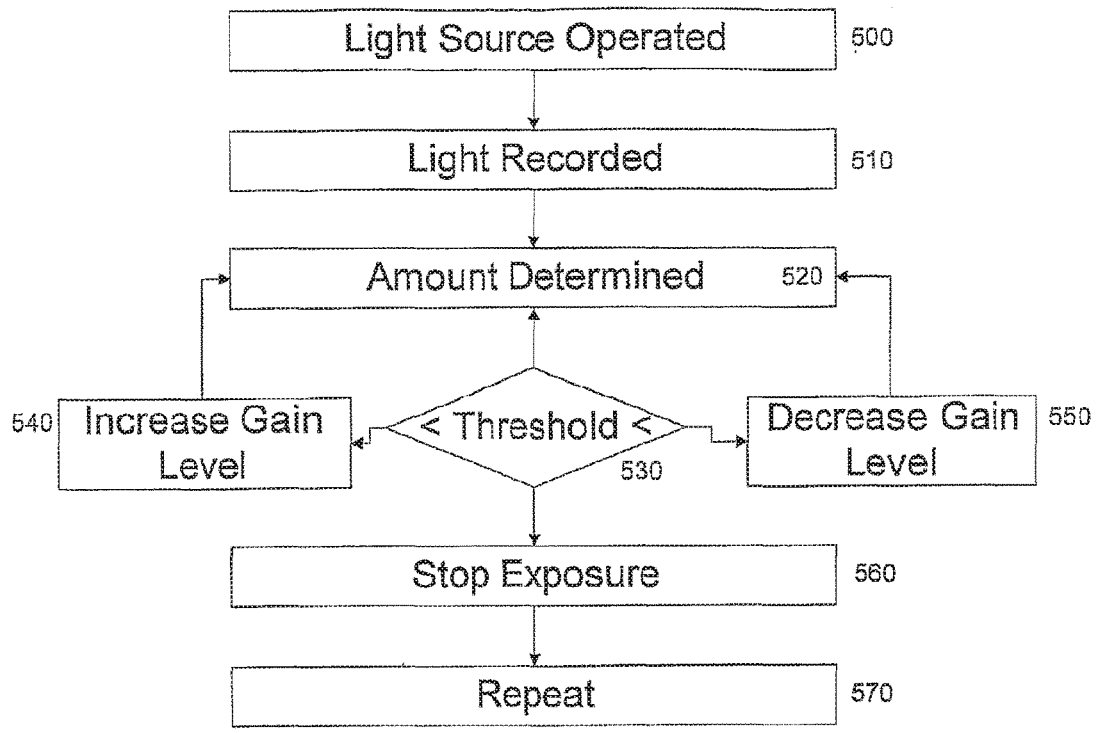
FIG. 16A depicts a series of steps of a method according to an embodiment of the present invention.
FIG. 16B depicts a series of steps of a method according to an alternate embodiment of the present invention.
FIG. 16C depicts a series of steps of a method according to an additional embodiment of the present invention.
Figure 16:
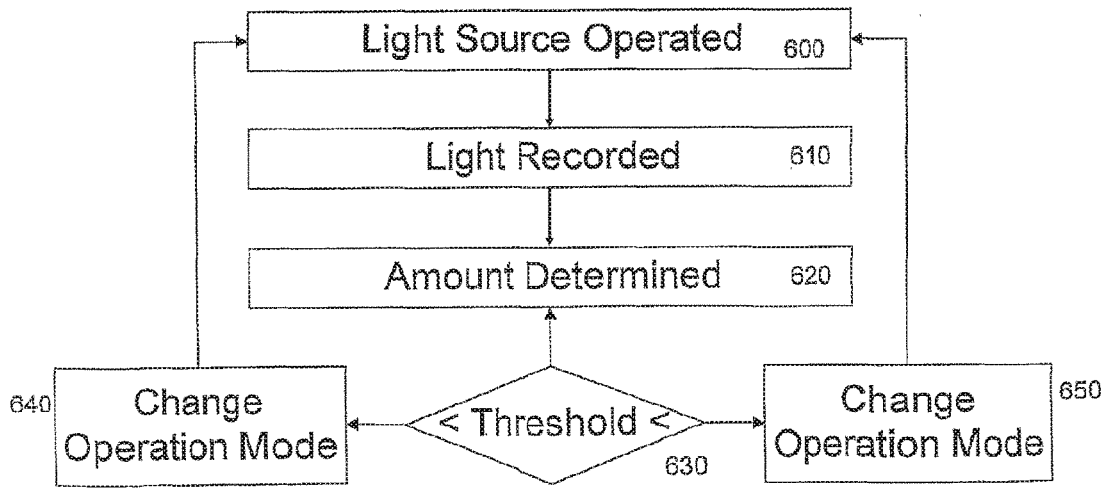
Figure 16:
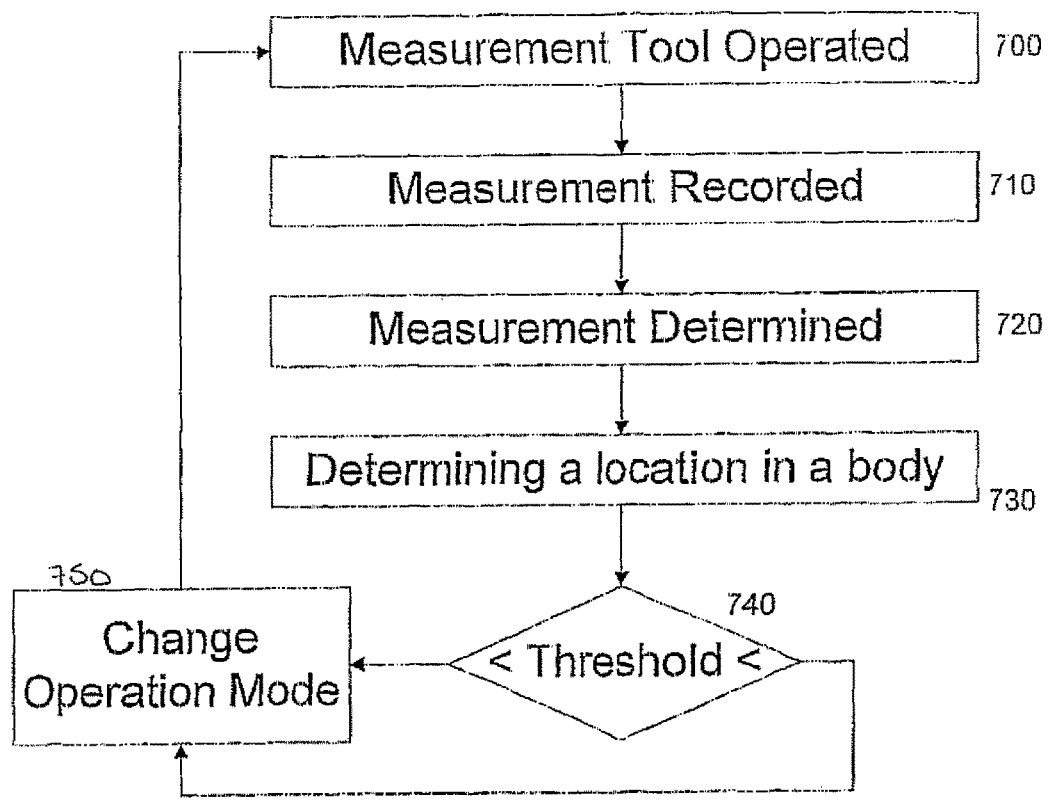

FIG. 16A depicts a series of steps of a method for determine a necessary image gain level during an exposure period, according to an embodiment of the present invention. In alternate embodiments, other steps, and other series of steps, may be used.

In step 500, a device, such as an in-vivo imaging device, turns on a light source.

In step 510, which may be a short sampling period, the device records (and possibly integrates) the amount of light received to at least one light measuring element. This may be, for example, to a sensor on the device, or possibly to an external sensor.

In step 520, the device determines the amount of light recorded.

In step 530, if the amount of light recorded, for example, by a portion of the frame's pixels is less than a certain pre-determined value (saturation threshold).

In step 540, the image gain level may be increased, and the device may continue exposure (or other parameters, such as light level etc.) until saturation is attained 560. In this case, step 520 may be repeated at a subsequent time interval.

In step 550, where the amount of light recorded is more than a certain value (threshold), the image gain level may be decreased. Step 520 may be repeated at a subsequent time. At full saturation exposure may be stopped 560.

If the amount of light recorded is substantially equivalent to a determined saturation threshold (close in value to such a threshold such that the amount of light exposed can be assumed to be sufficient), a current gain level or light level etc., may be maintained and the exposure may be stopped when full saturation occurs, or until a maximum exposure time ($T_M$) is reached, whichever is first to occur. The process may then be repeated 570 for subsequent frames.

In step 570, the above process is repeated from step 500, as, the device may operate across a series of imaging periods. However, the method need not be repeated.

According to one embodiment steps 500 to 520 may be complemented or replaced by a step wherein data from an environmental monitoring tool is analyzed, to determine if one or more particular data measurements, such as pH level, temperature level etc., are above, below or equal to a threshold for the particular measurement(s), or to one or more previous measurements. The results of such a comparison may be used to determine whether an environmental change has occurred, and whether an appropriate gain level change is in order. For example, an in vivo capsule may be adapted to carry multiple measurement tools for measuring different aspects in the environment, including a light level indicator and a pH indicator. In frame A the capsule may have measured levels i and ii using the two indicators listed above. In a second frame B it may be determined, for example, that both parameters i and ii have changed substantially from their measurements in frame 1. In the case where the light level indicator reflects a darkening of the environment, and the pH indicator indicate a higher acidity, it may be determined that the capsule has both entered the body (a darker environment) and entered the stomach (increased acidity).

FIG. 16B depicts a series of steps of a method for determining when an in vivo device has entered an area with different illumination, according to an embodiment of the present invention. In alternate embodiments, other steps, and other series of steps, may be used.

In step 600, a device, such as an in-vivo imaging device, turns on (operates) a light source.

In step 610, the device records (and possibly integrates) the amount of light received to a light measurement element. This may be, for example, part of the imager, a sensor on the device, or possibly to an external sensor.

In step 620, the device determines the amount of light recorded. Furthermore, the device may calculate this amount of light recorded in relation to a saturation threshold or any other threshold, to determine a possible location of the device based on the amount of light recorded. For example, if the light recorded in a first frame is above a saturation threshold of, for example, 15 pixels out of the frame, this indicates that saturation has easily been attained, and the device is assumed to be outside the body (in a light environment). If the light recorded in a second frame is below the same saturation threshold of, for example, 15 pixels out of the frame, this indicates that saturation has not been attained, and the device is assumed to be inside the body (in a dark environment).

In step 630, a decision may be taken to change operation mode of the device, depending on the amount of light recorded relative to a threshold value.

In step 640, for example, if the amount of light recorded is less than a certain value (threshold), indicating that the device is located in a darker area, the device may change the mode of operation 640 to reflect this darker environment. For example, the device may be configured to start operating in a fast-mode for a period of 10 minutes after entering the body, to enable fast imaging of the esophagus area. After determining that the device has entered the body, the timer may be initiated, so that after 10 minutes the device will change into a slower mode for the remainder of the procedure.

In step 650, for example, if the amount of light recorded is more than a certain value (threshold), indicating that the device is located in a lighter area, the device may change the mode of operation 650 to reflect this lighter environment.

FIG. 16C depicts a series of steps of a method for determining an in vivo device's location, according to an embodiment of the present invention. In alternate embodiments, other steps, and other series of steps, may be used.

In step 700, a device, such as an in-vivo imaging device, operates at least one environmental measuring device, such as, for example, a pH level sensor and a light detection meter.

In step 710, the device records a measurement, such as pH level for example, received to the measurement device. This measurement device may be, for example, a sensor on or in the device and/or an external sensor.

In step 720, the device determines the quantity and/or quality of the measurement recorded.

In step 730, the device may determine a location in a body based on the measurement data recorded, as compared with a threshold value or previous measurements etc. For example, if the pH level in a first frame is above a saturation threshold of, for example 7 on the pH scale, this indicates that the device is in a non-acidic environment, and may be assumed to be in the throat area (in an acidic-neutral environment). If the pH level recorded in a second frame is below the same threshold of, for example, 7 on the pH scale, this indicates that the device is in a more acidic environment, and may be assumed to be in the stomach or intestine area, depending on the pH level recorded.

In step 740, a decision may be taken to change operation mode of the device, depending on the measurement data recorded relative to a threshold or alternative value.

In step 750, for example, if the amount of measurement data quantity and/or quality is more or less than a certain value (threshold or other value), indicating (or verifying) that the device is located in a different area, the device may change the mode of operation to reflect this new environment.

The results of the above processes may be used to determine whether environmental conditions have substantially changed, based on results from various optional monitoring and/or measuring tools. The change required to be defined as "substantial" or "significant" may be determined for each case or by manufacture.

Typically, the various embodiments discussed herein may be implemented in a device such as device 30 (FIG. 2); however, such embodiments may be implemented in a variety of imaging or sensing devices, varying in structure. The various functions and processes described above, including but not limited to processing, monitoring, measuring, analyzing, defining, tracking, comparing, computing, commanding, stopping exposure, increasing gain, decreasing gain, increasing exposure, decreasing exposure, changing mode etc. may be executed by, for example, a processor unit (e.g., 36 in FIG. 2). These functions or processes may additionally and/or alternatively be implemented by the processor unit 36 alone, by alternative units, such as illumination control unit 40, telemetry unit 34, light sensing units 42, imaging unit 32 etc., or any combination of units. The methods and processes described may also be embodied in other sensing devices having other structures and other components. Alternately, part or all of the analysis or control involved in the various methods presented may be performed by an external workstation or processing unit.

It will be appreciated by those skilled in the art that while the invention has been described with respect to a limited number of embodiments, many variations, modifications, combinations and other applications of the invention may be made which are within the scope and spirit of the invention.

The invention claimed is:

1. A method of operating a swallowable in-vivo imaging capsule, the capsule comprising a light source and an imager, the method comprising across a plurality of imaging periods, each imaging period including a sampling period and a subsequent illumination period:
   during the sampling period, operating the light source to provide illumination and recording an amount of light reflected to the imager;
   calculating, based on the amount of light recorded, a calculated intensity or duration of the illumination to be provided during the illumination period; and
   during the illumination period, operating the light source to provide illumination at said calculated intensity or duration.

2. The method of claim 1 wherein each imaging period comprises a dark period during which pixel information is read.

3. The method of claim 1 comprising scanning the imager to acquire an image.

4. The method of claim 1 wherein the recording is based on a signal from the imager.

5. A swallowable in-vivo imaging capsule, comprising:
   a light source;
   an imager; and
   a controller, the controller to, across a plurality of imaging periods, each imaging period including a sampling period a subsequent illumination period:

during the sampling period, operate the light source to provide illumination and record an amount of light reflected to the imager;

calculate, based on the amount of light recorded, a calculated intensity or duration of the illumination to be provided during the illumination period; and during the illumination period, cause the light source to provide illumination at said calculated intensity or duration.

6. The capsule of claim 5 wherein each imaging period comprises a dark period during which pixel information is read.

7. The capsule of claim 5 wherein the controller is to scan the imager to acquire an image.

8. The capsule of claim 5 wherein a recording of the light by the controller is based on a signal from the imager.

9. A method of operating a swallowable in-vivo imaging capsule, the swallowable in-vivo imaging capsule comprising a plurality of LEDs an imager, the method comprising across a plurality of imaging periods, each imaging period including an illumination period and a sampling period:

during a sampling period operating the plurality of LEDs and recording an amount of light reflected to the swallowable in-vivo imaging capsule;

calculating, based on the amount of reflected light, a calculated intensity or duration of the illumination to be provided during an illumination period; and during the illumination period, providing illumination using the plurality of LEDs at said calculated intensity or duration.

10. The method of claim 9 wherein each imaging period comprises a dark period during which pixel information is read.

11. The method of claim 9 comprising scanning the imager to acquire an image.

12. The method of claim 9 wherein the recording is based on a signal from the imager.

* * * * *